US010152568B2

(12) United States Patent
Lo et al.

(10) Patent No.: US 10,152,568 B2
(45) Date of Patent: Dec. 11, 2018

(54) NONINVASIVE PRENATAL GENOTYPING OF FETAL SEX CHROMOSOMES

(75) Inventors: Yuk Ming Dennis Lo, Kowloon (HK); Wai Kwun Rossa Chiu, Shatin (HK); Kwan Chee Chan, Kowloon (HK); Bo Yin Tsui, Ma On Shan (CN)

(73) Assignee: The Chinese University of Hong Kong, Shatin, New Territories (HK)

( * ) Notice: Subject to any disclaimer, the term of this patent is extended or adjusted under 35 U.S.C. 154(b) by 907 days.

(21) Appl. No.: 13/978,358

(22) PCT Filed: Jan. 5, 2012

(86) PCT No.: PCT/IB2012/000015
§ 371 (c)(1),
(2), (4) Date: Oct. 3, 2013

(87) PCT Pub. No.: WO2012/093331
PCT Pub. Date: Jul. 12, 2012

(65) Prior Publication Data
US 2014/0019064 A1    Jan. 16, 2014

Related U.S. Application Data

(60) Provisional application No. 61/430,032, filed on Jan. 5, 2011, provisional application No. 61/475,632, filed on Apr. 14, 2011.

(51) Int. Cl.
*G06F 19/18* (2011.01)
*C12Q 1/6883* (2018.01)

(52) U.S. Cl.
CPC ........... *G06F 19/18* (2013.01); *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,440,706 B1 | 8/2002 | Vogelstein et al. | |
| 6,753,147 B2 | 6/2004 | Vogelstein et al. | |
| 7,727,720 B2 | 6/2010 | Dhallan | |
| 2003/0180765 A1 | 9/2003 | Traverso et al. | |
| 2004/0137470 A1 | 7/2004 | Dhallan | |
| 2005/0130176 A1 | 6/2005 | Vogelstein et al. | |
| 2007/0202525 A1 | 8/2007 | Quake et al. | |
| 2007/0207466 A1 | 9/2007 | Cantor | |
| 2009/0087847 A1 | 4/2009 | Lo et al. | |

FOREIGN PATENT DOCUMENTS

| | | |
|---|---|---|
| JP | 2001-513648 A | 9/2001 |
| JP | 2010-534068 A | 11/2010 |
| JP | 2010-534069 A | 11/2010 |
| WO | 98/39474 A1 | 9/1998 |
| WO | WO 2007/092473 A2 | 8/2007 |
| WO | 2009/013492 A1 | 1/2009 |
| WO | 2009/013492 A1 | 6/2009 |
| WO | 2010/018465 A1 | 2/2010 |

OTHER PUBLICATIONS

Fan et al. Noninvasive diagnosis of fetal aneuploidy by shotgun sequencing DNA from maternal blood Proceedings of the National Academy of Sciences vol. 105, pp. 16266-16271 (2008).*
Lee et al. The obstetric and gynaecological management of women with inherited bleeding disorders—review with guidelines produced by a taskforce of UK Haemophilia Centre Doctors Organization Haemophilia vol. 12, pp. 301-336 (2006).*
Fan et al. 2010 Sensitivity of Noninvasive Prenatal Detection of Fetal Aneuploidy from Maternal Plasma Using Shotgun Sequencing Is Limited Only by Counting Statistics PLoS One vol. 5, article e10439 (2010).*
Office Action (English Translation) dated Jul. 31, 2015 in Japanese Patent Application No. 2013-547929, 8 pages.
Chiu, R., et al., "Application of fetal DNA in maternal plasma for noninvasive prenatal diagnosis," *Expert Review of Molecular Diagnostics*, vol. 2(1), pp. 32-40 (Jan. 2002).
Lun, F., et al., "Noninvasive prenatal diagnosis of monogenic diseases by digital size selection and relative mutation dosage on DNA in maternal plasma," *Proceedings of the National Academy of Sciences of the USA*, vol. 105(50), pp. 19920-19925 (Dec. 16, 2008).
Tsui, N., et al. "Noninvasive prenatal diagnosis of hemophilia by microfluidics digital PCR analysis of maternal plasma DNA," *Blood*, vol. 117(13), pp. 3684-3691 (Mar. 31, 2011).
International Search Report of PCT/IB2012/000015, dated Apr. 27, 2012, 4 pgs.
Written Opinion of International Searching Authority of PCT/IB2012/000015, dated Apr. 27, 2012, 6 pgs.

(Continued)

*Primary Examiner* — John S Brusca
(74) *Attorney, Agent, or Firm* — Kilpatrick Townsend & Stockton LLP

(57) ABSTRACT

Methods, apparatuses, and system are provided for analyzing a maternal sample to determine whether a male fetus of a pregnant female has inherited an X-linked mutation from the mother. A percentage of fetal DNA in the sample is obtained, and cutoff values for the two possibilities (fetus inherits mutant or normal allele) are determined. A proportion of mutant alleles relative to a normal allele on the X-chromosome can then be compared to the cutoff values to make a classification of which allele is inherited. Alternatively, a number of alleles from a target region on the X-chromosome can be compared to a number of alleles from a reference region on the X-chromosome to identify a deletion or amplification. The fetal DNA percentage can be computed by counting reactions with a fetal-specific allele, and correcting the number to account for a statistical distribution among the reactions.

49 Claims, 17 Drawing Sheets
Specification includes a Sequence Listing.

(56) References Cited

OTHER PUBLICATIONS

Chang, Hsueh-Wei et al.; "Assessment of Plasma DNA Levels, Allelic Imbalance, and CA 125 as Diagnostic Tests for Cancer"; 2002, *Journal of the National Cancer Institute*, vol. 94, No. 22, pp. 1697-1703.
Chiu, R., et al., "Noninvasive prental diagnosis of fetal chromosomal aneuploidy by massively parallel genomic sequencing of DNA in maternal plasma," *PNAS*, vol. 105(51), pp. 20458-20463 (Dec. 23, 2008).
Dhallan, R., et al., "A Non-Invasive Test for Prenatal Diagnosis Based on Fetal DNA Present in Maternal Blood: A Preliminary Study," www.thelancet.com, Feb. 2, 2007, 8 pages.
Diehl, Frank et al.; "Detection and quantification of mutations in the plasma of patients with colorectal tumors"; 2005, *PNAS*, vol. 102, No. 45, pp. 16368-16373.
El Karoui, Noureddine et al.; "Getting more from digital SNP data"; 2006, *Statistics in Medicine*, vol. 25, pp. 3124-3133.
Lo Y, et al., "Plasma placental RNA allelic ratio permits noninvasive prenatal chromosomal aneuploidy detection," *Nature Medicine*, vol. 13(2), Feb. 2007, pp. 218-223.
Lo, Y., et al., "Digital PCR for the molecular detection of fetal chromosomal aneuploidy," *PNAS*, vol. 104(32), pp. 13116-13121 (Aug. 7, 2007).
Lo, Y., et al., "Prenatal diagnosis: progress through plasma nucleic acids," *Nature Reviews Genetics*, vol. 8, Jan. 2007, pp. 71-77.
Ottesen, Elizabeth A. et al.; "Microfluidic Digital PCR Enables Multigene Analysis of Individual Environmental Bacteria"; 2006, *Science*, vol. 314, pp. 1464-1467.
Panhard, Xaviere et al.; "Constructions of a global score quantifying allelic imbalance among biallelic SIDP markers in bladder cancer"; 2003, *Statistics in Medicine*, vol. 22, pp. 3771-3779.
Pohl, Gudrun et al.; "Principle and applications of digital PCR"; 2004, *Expert Rev. Mol. Diagn.*, vol. 4, No. 1, pp. 41-47.
Rubben, A., et al., "Somatic deletion of the NFI gene in a neurofibromatosis type I-associated malignant melanoma demonstrated by digial PCR," *Molecular Cancer*, vol. 5, p. 36(1-9) (2006).
Shih, I-M., et al., "Evidence that genetic instability occurs at an early stage of colorectal tumorigenesis," *Cancer Research*, 2001, vol. 61, pp. 818-822.
Tong, Y.T., "Noninvasive prenatal detection of fetal trisomy 18 by epigenetic allelic ratio analysis in maternal plasma: Theoretical and empirical considerations," *Clinical Chemistry*, 2006, vol. 52, pp. 2194-2202.
Vogelstein, Bert et al.; "Digital PCR"; 1999, *PNAS*, vol. 96, pp. 9236-9241.
Warren, Luigi et al.; "Transcription factor profiling in individual hematopoietic progenitors by digital RT-PCR"; 2006, *PNAS*, vol. 103, No. 47, pp. 17807-17812.
Zhou, Wei et al.; "Counting alleles reveals a connection between chromosome 18q loss and vascular invasion"; 2001, *Nature Biology*, vol. 19, pp. 78-81.
Zhou, Wei et al.; "Counting alleles to predict recurrence of early-stage colorectal cancers"; 2002, *The Lancet*, vol. 359, pp. 219-225.
Lun, et al., "Microfluidics digital PCR Reveals a Higher than expected fraction of fetal DNA in maternal plasma", Clinical Chemistry, vol. 54, No. 10, Oct. 1, 2008, pp. 1664-1672.
Office Action (English Translation) dated Apr. 19, 2016 in Japanese Patent Application No. 2013-547929, 8 pages.
Supplementary European Search Report dated Nov. 25, 2015 in European Patent Application No. 12732095.0, 9 pages.
Dhallan, R., et al., Methods to increase the percentage of free fetal DNA recovered from the maternal circulation,: JAMA, Mar. 3, 2004, vol. 291, No. 9, pp. 1114-1119.
Ragni, Margaret V.; "Prenatal diagnosis by droplet digital PCR"; Blood; Jul. 20, 2017; vol. 103, No. 3; pp. 240-241 (3 pages).
Lee, C.A. et al.; "The obstetric and gynaecological management of women with inherited bleeding disorders—review with guidelines produced by a taskforce of UK Haemophilia Centre Doctors' Organization"; Haemophilia; 2006; vol. 12, Issue 4; pp. 301-336.

* cited by examiner

| Disease type | Maternal genotype | Fetal genotype | Maternal plasma DNA — Total DNA alleles in maternal plasma = 100 GE [1]; Fetal DNA percentage = 10% [1] | | | | | | |
|---|---|---|---|---|---|---|---|---|---|
| | | | Maternal-derived alleles Total maternal alleles = 90 GE | | Fetal-derived alleles Total fetal alleles = 10 GE | | (maternal + fetal) alleles | | M:N ratio |
| | | | M (copies) | N (copies) | M (copies) | N (copies) | M (copies) | N (copies) | |
| X-linked diseases | [N]—XX [M]—XX | [N]—XY | 90 [2] | 90 [2] | 0 [3] | 10 [3] | 90 | 100 | 0.90 : 1 |
| | | [M]—XY | 90 | 90 | 10 | 0 | 100 | 90 | 1.11 : 1 |

[1] To illustrate the calculation, a maternal plasma sample containing a total of 100GE of DNA with 10% fetal DNA was used.
[2] For the maternal genome, 1GE contains 2 copies of the alleles, i.e., one copy each of the M and the N allele.
[3] For the fetal genome, 1GE contains 1 copy of the X-linked allele, i.e., one copy of either the M or the N allele.
GE, Genome-equivalent; M, mutant allele; N, wild-type allele.

Maternal plasma DNA
Total DNA alleles in maternal plasma = 100 GE [1]
Fetal DNA proportion = 10% [1]

| Mutation type | Maternal genotype | Fetal genotype | Maternal-derived alleles [2] Total maternal alleles = 90 GE | | Fetal-derived alleles [3] Total fetal alleles = 10 GE | | (maternal + fetal) alleles | | T : ZFX | |
|---|---|---|---|---|---|---|---|---|---|---|
| | | | T (copies) | ZFX (copies) | T (copies) | ZFX (copies) | T (copies) | ZFX (copies) | Maternal genome | Maternal plasma |
| Deletion | X X | X Y | 90 | 180 | 10 | 10 | 100 | 190 | 0.5 : 1 | 0.53 : 1 |
| | | X Y | | | 0 | 10 | 90 | 190 | | 0.47 : 1 |
| Duplication | X X | X Y | 270 | 180 | 10 | 10 | 280 | 190 | 1.5 : 1 | 1.47 : 1 |
| | | X Y | | | 20 | 10 | 290 | 190 | | 1.53 : 1 |

[1] To illustrate the calculation, a maternal plasma sample containing a total of 100GE of DNA with 10% fetal DNA was used.
[2] For the maternal genome, 1GE contains 2 copies of ZFX, as well as 1 copy of the target allele in the deleted region, or 3 copies of the target allele in the duplicated region.
[3] For the fetal genome, 1GE contains 1 copy of ZFX, and 1 copy of the target allele for the normal fetus. For fetus inherits the deleted or the duplicated locus, 1 GE corresponds to 0 and two copies of the target allele, respectively.
GE, genome-equivalent; T, the target molecules.

| Sample | Gestation (weeks) | Affected gene | Mutation[1] | Severity of hemophilia | Fetal information | |
|---|---|---|---|---|---|---|
| | | | | | Sex | Hemophilia status |
| H9 | 36 | F9 | c.874delC (p.Gln292Lysfs) | Severe | Male | Affected |
| H12a[2] | 18 | F8 | c.6278A>G (p.Asp2093Gly) | Mild | Male | Affected |
| H12b | 34 | | | | | |
| H15a[2] | 34 | F9 | c.1144T>C (p.Cys382Arg) | Severe | Male | Affected |
| H15b | 38 | | | | | |
| H17 | 28 | F8 | c.826G>A (p.Val276Met) | Mild | Male | Unaffected |
| H25a[2] | 23 | F9 | c.802T>A (p.Cys268Ser) | Moderate/ Severe | Male | Affected |
| H25b | 32 | | | | | |
| H26a[2] | 11 | F8 | c.1171C>T (p.Arg391Cys) | Severe | Male | Unaffected |
| H26b | 23 | | | | | |
| H30a[2] | 32 | F9 | c.1069G>A (p.Gly357Arg) | Moderate/ Severe | Male | Unaffected |
| H30b | 40 | | | | | |

[1] Mutation nomenclature is based on the guidelines of the Human Genome Variation Society. The reference sequences for hemophilia A and B mutations are F8 mRNA variant 1 (Genbank accession NM_000132.3) and F9 mRNA (NM_000133.3), respectively. Nucleotide position +1 corresponds to the A nucleotide of the ATG translation initiation codon. Amino acid changes deduced from the DNA mutations are shown in the brackets. The reference sequences correspond to coagulation factor VIII isoform a precursor (NP_000123.1) and coagulation factor IX preproprotein (NP_000124.1), respectively. The translation initiator methionine is numbered as position +1.

[2] Peripheral blood samples were taken on two occasions from the same women during their pregnancies.

FIG. 9

| Locus | | Sequence | Final concentration, nM | Annealing temperature |
|---|---|---|---|---|
| ZFY/X | F-primer | 5'-CAAGTGCTGGACTCAGATGTAACTG-3' | 900 | 57°C |
| | R-primer | 5'-TGAAGTAATGTCAGAAGCTAAAACATCA-3' | 900 | |
| | X-probe | 5'-(VIC)TCTTTAGCACATTGCA(MGBNFQ)-3' | 100 | |
| | Y-probe | 5'-(FAM)TCTTTACCACACTGCAC(MGBNFQ)-3' | 100 | |
| Rs6528633 | F-primer | 5'-GGAAGACCAAAAAGGGATAAAGG-3' | 900 | 57°C |
| | R-primer | 5'-CACCCTACTCCCAGCCAATTT-3' | 900 | |
| | T-probe | 5'-(VIC)TGAGATATGATATGGTCATG(MGBNFQ)-3' | 200 | |
| | A-probe | 5'-(FAM)TGAGATATGATAAGGTCATG(MGBNFQ)-3' | 179 | |
| F8 c.826G>A | F-primer | 5'-TGGATGCCACAGGAAATCAG-3' | 900 | 58°C |
| | R-primer | 5'-CTTCAGGAGTGGTGCCCATT-3' | 900 | |
| | G-probe | 5'-(VIC)CTATTGGCATGTGATTG(MGBNFQ)-3' | 200 | |
| | A-probe | 5'-(FAM)CTATTGGCATATGATTG(MGBNFQ)-3' | 179 | |
| F8 c.1171C>T | F-primer | 5'-TGGATGTGGTCAGGTTTGATGA-3' | 900 | 58°C |
| | R-primer | 5'-TTTTAGGATGCTTCTTGGCAACT-3' | 900 | |
| | C-probe | 5'-(FAM)CTGAGCGAATTTGGATA(MGBNFQ)-3' | 150 | |
| | T-probe | 5'-(VIC)CTGAGCAAATTTGGAT(MGBNFQ)-3' | 200 | |
| F8 c.6278A>G | F-primer | 5'-TTTCAGGAGGTAGCACATACATTT-3' | 900 | 56°C |
| | R-primer | 5'-TGCCGTGAATAATCATTGGT-3' | 900 | |
| | A-probe | 5'-(VIC)CAACAGATCCACCTAC(MGBNFQ)-3' | 300 | |
| | G-probe | 5'-(FAM)AACAGACCCACCTAC(MGBNFQ)-3' | 269 | |
| F9 c.802T>A | F-primer | 5'-TCTGTGGAGGCTCTATCGTTAATG-3' | 900 | 58°C |
| | R-primer | 5'-ACCTGCGACAACTGTAATTTTAACAC-3' | 900 | |
| | T-probe | 5'-(VIC)TGCCCACTGTGTTGA(MGBNFQ)-3' | 220 | |
| | A-probe | 5'-(FAM)CTGCCCACAGTGTTG(MGBNFQ)-3' | 100 | |
| F9 c.874delC | F-primer | 5'-TGTCGCAGGTGAACATAATATTGA-3' | 900 | 58°C |
| | R-primer | 5'-GGTGAGGAATAATTCGAATCACATT-3' | 900 | |
| | C-probe | 5'-(VIC)ACATACAGAGCAAAAG(MGBNFQ)-3' | 120 | |
| | del-probe | 5'-(FAM)CATACAGAGAAAAGC(MGBNFQ)-3' | 120 | |
| F9 c.1069G>A | F-primer | 5'-CCTCAAATTTGGATCTGGCTA-3' | 900 | 58°C |
| | R-primer | 5'-GCTGATCTCCCTTTGTGGAA-3' | 900 | |
| | G-probe | 5'-(VIC)ACTCTTCCCCAGCCAC(MGBNFQ)-3' | 179 | |
| | A-probe | 5'-(FAM)ACTCTTCTCCAGCCACT(MGBNFQ)-3' | 200 | |
| F9 c.1144T>C | F-primer | 5'-CAGTACCTTAGAGTTCCACTTGTTGAC-3' | 900 | 58°C |
| | R-primer | 5'-CATGTTGTTATAGATGGTGAACTTTGTAG-3' | 900 | |
| | T-probe | 5'-(VIC)CCACATGTCTTCG(MGBNFQ)-3' | 200 | |
| | C-probe | 5'-(FAM)AGCCACACGTCTTC(MGBNFQ)-3' | 130 | |

VIC and FAM, fluorescent reporter dyes; MGBNFQ, minor groove binding nonfluorescent quencher.

FIG. 10

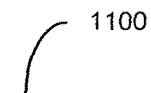

| Sample | Gestation (weeks) | SNP genotype[1] | | Digital PCR result | | | Fetal %[3] | $m_r$[4] | SPRT Classificat-ion[5] |
|---|---|---|---|---|---|---|---|---|---|
| | | Mother | Fetus | Total wells | A count[2] | T count[2] | | | |
| M5193P | 17 3/7 | AT | A | 4590 | 410 | 335 | 7.5 | 0.09 | A |
| M5280P | 17 4/7 | AT | A | 4590 | 204 | 144 | 10.7 | 0.05 | A |
| M5269P | 19 2/7 | AT | T | 4590 | 337 | 409 | 11.2 | 0.08 | T |
| M5297P | 19 3/7 | AT | A | 13770[6] | 1482 | 1368 | 5.4 | 0.11 | A |
| M5244P | 22 6/7 | AT | T | 4590 | 139 | 163 | 8.5 | 0.03 | T |
| M5240P | 38 2/7 | AT | T | 4590 | 396 | 484 | 23.7 | 0.09 | T |
| M5241P | 38 2/7 | AT | T | 4590 | 706 | 920 | 13.9 | 0.17 | T |
| M4817P | 38 4/7 | AT | A | 4590 | 502 | 425 | 17.2 | 0.12 | A |
| M4847P | 39 3/7 | AT | A | 4590 | 379 | 312 | 14.9 | 0.09 | A |
| M4846P | 40 | AT | A | 4590 | 700 | 516 | 17.5 | 0.17 | A |

[1]SNP genotypes were determined by mass spectrometry.
[2]A count, number of wells positive for the A allele. T count, number of wells positive for the T allele.
[3]Fetal DNA percentages were determined by the digital ZFY/X assay.
[4]Average reference template concentration per PCR well. The reference template referred to the allele with the lesser count in each sample.
[5]Classification of fetal genotypes by SPRT.
[6]M5297P was unclassifiable by SPRT with data from the first 4590-well digital PCR set. Two additional 4590-well digital PCR sets were performed after which classification could be made.

FIG. 11

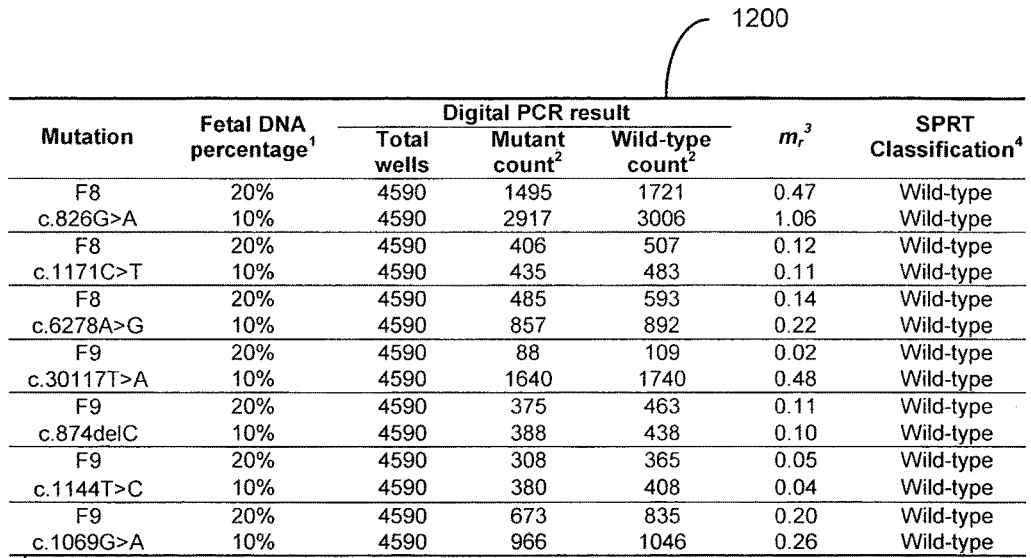

| Mutation | Fetal DNA percentage[1] | Digital PCR result | | | $m_r$[3] | SPRT Classification[4] |
|---|---|---|---|---|---|---|
| | | Total wells | Mutant count[2] | Wild-type count[2] | | |
| F8 c.826G>A | 20% | 4590 | 1495 | 1721 | 0.47 | Wild-type |
| | 10% | 4590 | 2917 | 3006 | 1.06 | Wild-type |
| F8 c.1171C>T | 20% | 4590 | 406 | 507 | 0.12 | Wild-type |
| | 10% | 4590 | 435 | 483 | 0.11 | Wild-type |
| F8 c.6278A>G | 20% | 4590 | 485 | 593 | 0.14 | Wild-type |
| | 10% | 4590 | 857 | 892 | 0.22 | Wild-type |
| F9 c.30117T>A | 20% | 4590 | 88 | 109 | 0.02 | Wild-type |
| | 10% | 4590 | 1640 | 1740 | 0.48 | Wild-type |
| F9 c.874delC | 20% | 4590 | 375 | 463 | 0.11 | Wild-type |
| | 10% | 4590 | 388 | 438 | 0.10 | Wild-type |
| F9 c.1144T>C | 20% | 4590 | 308 | 365 | 0.05 | Wild-type |
| | 10% | 4590 | 380 | 408 | 0.04 | Wild-type |
| F9 c.1069G>A | 20% | 4590 | 673 | 835 | 0.20 | Wild-type |
| | 10% | 4590 | 966 | 1046 | 0.26 | Wild-type |

[1] Fetal DNA was mixed in the specified percentages with maternal DNA. Fetal DNA was obtained from the placenta of a normal male fetus. Maternal DNA was obtained from the blood cells of pregnant women heterozygous for the corresponding mutations.

[2] Mutant count, number of wells positive for the mutant allele. Wild-type count, number of wells positive for the wild-type allele.

[3] Average reference template concentration per PCR well. The reference template referred to the allele with the lesser count in each sample.

[4] SPRT classification of "fetal genotypes", which was mimicked by the normal placental DNA in the artificial mixtures.

FIG. 12

| Plasma sample | Fetal hemophilia status | Digital PCR result | | | Fetal %[2] | $m_r^3$ | SPRT Classification[4] |
|---|---|---|---|---|---|---|---|
| | | Total wells | Mutant count[1] | Wild-type count[1] | | | |
| H9 | Affected | 4590 | 1022 | 801 | 14.8 | 0.19 | Mutant |
| H26a | Unaffected | 9180 | 1590 | 1710 | 3.8 | 0.21 | Wild-type |
| H26b | Unaffected | 4590 | 590 | 650 | 6.8 | 0.15 | Wild-type |
| H15a | Affected | 4590 | 573 | 435 | 10.5 | 0.10 | Mutant |
| H15b | Affected | 4590 | 2506 | 1956 | 10.7 | 0.56 | Mutant |
| H17 | Unaffected | 4590 | 329 | 342 | 14.0 | 0.08 | Wild-type |
| H30a | Unaffected | 4590 | 611 | 780 | 18.2 | 0.19 | Wild-type |
| H30b | Unaffected | 4590 | 1839 | 2017 | 11.4 | 0.58 | Wild-type |
| H25a | Affected | 9180 | 1160 | 1108 | 4.6 | 0.13 | Mutant |
| H25b | Affected | 4590 | 223 | 166 | 15.0 | 0.04 | Mutant |
| H12a | Affected | 9180 | 511 | 464 | 9.0 | 0.05 | Mutant |
| H12b | Affected | 4590 | 293 | 230 | 25.1 | 0.05 | Mutant |

[1]Mutant count, number of wells positive for the mutant allele. Wild-type count, number of wells positive for the wild-type allele.
[2]Fetal DNA percentages were determined by the digital ZFY/X assay.
[3]Average reference template concentration per PCR well. The reference template referred to the allele with the lesser count in each sample.
[4]Classification of fetal genotypes by SPRT.

FIG. 13

| Mutation | Plasma sample | Gestation (weeks) | Digital PCR result | | | Fetal %[3] |
|---|---|---|---|---|---|---|
| | | | Total wells | Mutant count[1,2] | Wild-type count[1] | |
| F8 c.826G>A | N1P | 26 | 4590 | 0 | 589 | 12.8 |
| | N10P | 36 | 4590 | 0 | 1541 | 17.9 |
| | N11P | 28 | 4590 | 0 | 587 | 10.0 |
| | N17P | 39 | 4590 | 0 | 2476 | 16.9 |
| | N21P | 30 | 4590 | 0 | 763 | 10.3 |
| F8 c.1171C>T | N1P | 26 | 4590 | 0 | 575 | 12.8 |
| | N10P | 36 | 4590 | 0 | 1346 | 17.9 |
| | N11P | 28 | 4590 | 0 | 583 | 10.0 |
| | N17P | 39 | 4590 | 1 | 2202 | 16.9 |
| | N21P | 30 | 4590 | 0 | 640 | 10.3 |
| F8 c.6278A>G | N2P | 37 | 4590 | 0 | 1584 | 14.0 |
| | N3P | 35 | 4590 | 0 | 737 | 18.3 |
| | N11P | 28 | 4590 | 0 | 406 | 10.0 |
| | N13P | 42 | 4590 | 0 | 587 | 29.8 |
| | N19P | 36 | 4590 | 0 | 623 | 18.6 |
| F9 c.802T>A | N1P | 26 | 3825 | 0 | 261 | 12.8 |
| | N10P | 36 | 4590 | 0 | 814 | 17.9 |
| | N11P | 28 | 4590 | 0 | 410 | 10.0 |
| | N17P | 39 | 4590 | 0 | 1406 | 16.9 |
| | N21P | 30 | 4590 | 0 | 549 | 10.3 |
| F9 c.874delC | N1P | 26 | 4590 | 0 | 457 | 12.8 |
| | N10P | 36 | 4590 | 0 | 1244 | 17.9 |
| | N11P | 28 | 4590 | 0 | 551 | 10.0 |
| | N17P | 39 | 4590 | 0 | 1767 | 16.9 |
| | N21P | 30 | 4590 | 0 | 606 | 10.3 |
| F9 c.1069G>A | N2P | 37 | 4590 | 0 | 2124 | 14.0 |
| | N3P | 35 | 4590 | 0 | 990 | 18.3 |
| | N11P | 28 | 4590 | 0 | 483 | 10.0 |
| | N17P | 39 | 4590 | 1 | 2112 | 16.9 |
| | N21P | 30 | 4590 | 1 | 708 | 10.3 |
| F9 c.1144T>C | N1P | 26 | 4590 | 1 | 613 | 12.8 |
| | N10P | 36 | 4590 | 0 | 1132 | 17.9 |
| | N11P | 28 | 4590 | 1 | 602 | 10.0 |
| | N17P | 39 | 4590 | 0 | 1808 | 16.9 |
| | N21P | 30 | 4590 | 2 | 597 | 10.3 |

[1] Mutant count, number of wells positive for the mutant allele. Wild-type count, number of wells positive for the wild-type allele.
[2] Some of the cases showed 1 or 2 wells positive for the mutant alleles. This might be due to cross hybridizations of the mutant fluorescent probes against the wild-type amplicons.
[3] Fetal DNA percentages were determined by the digital ZFY/X assay.

FIG. 15

NONINVASIVE PRENATAL GENOTYPING OF FETAL SEX CHROMOSOMES

CROSS-REFERENCES TO RELATED APPLICATIONS

The present application is a U.S. National Phase of PCT/IB2012/000015, filed Jan. 5, 2012, which claims priority from and is a non-provisional application of U.S. Provisional Application No. 61/430,032, entitled "Noninvasive Prenatal Genotyping Of Fetal Sex Chromosomes" by Lo et al. (008300US), filed Jan. 5, 2011; and U.S. Provisional Application No. 61/475,632, entitled "Noninvasive Prenatal Genotyping Of Fetal Sex Chromosomes" by Lo et al. (008301US), filed Apr. 14, 2011, the entire contents of which are herein incorporated by reference for all purposes.

This application is related to commonly owned U.S. patent application Ser. No. 12/178,116 entitled "Determining a Nucleic Acid Sequence Imbalance" by Lo et al. (005210US), filed Jul. 23, 2008, the disclosure of which is incorporated by reference in its entirety.

REFERENCE TO A SEQUENCE LISTING

The Sequence Listing written in file SequenceListing_080015-0828559.txt created on Nov. 28, 2016, 12,699 bytes, machine format IBM-PC, MS-Windows operating system, is hereby incorporated by reference in its entirety for all purposes.

BACKGROUND

Hemophilias A and B are caused by heterogeneous mutations in the genes on chromosome X that encode for the coagulation factor VIII (F8) (Kemball-Cook G, Tuddenham E G, *Nucleic Acids Res.*, 25:128-132 (1997)) and coagulation factor IX (F9) (Giannelli F, Green P M, Sommer S S, et al., *Nucleic Acids Res.*, 26:265-268 (1998)), respectively. There is a 25% chance for a pregnant hemophilia carrier to have an affected male fetus in each pregnancy. Prenatal diagnosis is an important aspect of reproductive choices for women in families with hemophilia (Lee C A, Chi C, Pavord S R, et al., *Haemophilia.*, 12:301-336 (2006)). In addition, it is also beneficial for appropriate obstetric management during labor and delivery as prolonged labor, invasive monitoring techniques and instrumental deliveries should be avoided in affected fetuses to minimize potential fetal and neonatal hemorrhagic complications (Lee C A, Chi C, Pavord S R, et al., *Haemophilia.*, 12:301-336 (2006)). Therefore, the development of a noninvasive prenatal diagnostic approach for hemophilia is beneficial to both obstetricians and hemophilia families.

Current prenatal diagnostic methods for sex-linked diseases are typically invasive and pose a risk to the fetus. The discovery of cell-free fetal DNA in maternal plasma has offered new opportunities for noninvasive prenatal diagnosis (Lo Y M D et al., *Lancet.*, 350:485-487 (1997); Lo Y M D, Chiu R W K, *Nat Rev Genet.*, 8:71-77 (2007)). A number of promising clinical applications have been developed based on the detection of paternally inherited genetic traits in maternal plasma. For example, the noninvasive detection of fetal sex and RHD status are useful for the clinical management of sex-linked diseases and RhD incompatibility (Bustamante-Aragones A et al., *Haemophilia.*, 14:593-598 (2008); Finning K et al., *BMJ.*, 336:816-818 (2008)). For monogenic diseases such as achondroplasia and β-thalassemia, the detection of the presence or absence of paternally inherited mutations in maternal plasma would allow one to diagnose autosomal dominant diseases or exclude autosomal recessive diseases of the fetuses, respectively (Saito H et al., *Lancet.*, 356:1170 (2000); Chiu R W K et al., *Lancet.*, 360:998-1000 (2002); Ding C et al., *Proc Natl Acad Sci USA.*, 101:10762-10767 (2004)).

Despite the rapid development of the field, it has remained difficult to detect fetal alleles that are inherited from mothers who are carriers for the mutations. The difficulty is caused by the coexistence of fetal and maternal DNA in maternal plasma, and the maternally inherited fetal allele is indistinguishable from the background maternal DNA (Lo Y M D, Chiu R W K, *Nat Rev Genet.*, 8:71-77 (2007)).

Therefore, it is desirable to provide accurate and efficient methods for determining whether a male fetus has inherited an X-linked mutation.

BRIEF SUMMARY

Methods, apparatuses, and system are provided for analyzing a maternal sample to determine whether a male fetus of a pregnant female has inherited an X-linked mutation from the mother. A percentage of fetal DNA in the sample is obtained, and cutoff values for the two possibilities (fetus inherits mutant or normal allele) are determined. A proportion of mutant alleles relative to a normal allele on the X-chromosome can then be compared to the cutoff values to make a classification of which allele is inherited. Alternatively, a number of alleles from a target region on the X-chromosome can be compared to a number of alleles from a reference region on the X-chromosome to identify a deletion or amplification. The fetal DNA percentage can be computed by counting reactions with a fetal-specific allele, and correcting the number to account for a statistical distribution among the reactions.

According to one embodiment, a method is provided for determining whether a male fetus of a pregnant female has an X-linked mutation. The pregnant female is heterozygous for a mutant and a normal allele at a locus on the X chromosome. Data is received from a plurality of reactions, each involving one or more nucleic acid molecules from a biological sample. The biological sample includes nucleic acid molecules from the pregnant female and from the male fetus. The data includes a first set of quantitative data indicating a first amount of the mutant allele at the locus and a second set of quantitative data indicating a second amount of the normal allele at the locus. A parameter is determined from the first amount and the second amount, where the parameter represents a relative amount between the first and second amounts. A percentage Pf of fetal nucleic acid molecules in the biological sample is obtained. A first cutoff value for determining whether the fetus has inherited the mutant allele at the locus is calculated, where the first cutoff value is derived at least from a first proportion of $k/(1+k-Pf)$, where k is a number of mutant alleles on a mutant chromosome of the pregnant female, k being an integer equal to or greater than one. A second cutoff value for determining whether the fetus has inherited the normal allele at the locus is calculated, where the second cutoff value is derived at least from a second proportion of $[k(1-Pf)]/[1+k-kPf]$. The parameter is compared to at least one of the first and second cutoff values to determine a classification of whether the fetus has inherited the mutant allele or the normal allele.

According to another embodiment, a method is provided for determining whether a male fetus of a pregnant female has an X-linked mutation. The pregnant female is heterozygous for a mutation and a normal allele at a target region on the X chromosome. The mutation is a deletion or an amplification of the target region. Data from a plurality of reactions is received. Each reaction involves one or more nucleic acid molecules from a biological sample. The biological sample includes nucleic acid molecules from the pregnant female and from the male fetus. The data includes a first set of quantitative data indicating a first amount of the nucleic acid molecules that are from the target region and a second set of quantitative data indicating a second amount of the nucleic acid molecules that are from a reference region on the X chromosome. A parameter is determined from the first amount and the second amount, where the parameter represents a relative amount between the first and second amounts. A percentage Pf of fetal nucleic acid molecules in the biological sample is obtained. A first cutoff value for determining whether the fetus has inherited the mutation is calculated. The first cutoff value is dependent on the percentage Pf. A second cutoff value for determining whether the fetus has inherited the normal allele is calculated. The second cutoff value is dependent on the percentage Pf. The parameter is compared to at least one of the first and second cutoff values to determine a classification of whether the fetus has inherited the mutation or the normal allele.

According to another embodiment, a method of obtaining a percentage Pf of fetal nucleic acid molecules in a biological sample from a female pregnant with a fetus. Data is received from a plurality of reactions. Each reaction involves a plurality of nucleic acid molecules from a biological sample, which includes nucleic acid molecules from the pregnant female and from the fetus. A first allele is detected in the reactions. The first allele is shared by the mother and fetus at a locus where the pregnant female is homozygous and the fetus is either heterozygous or hemizygous. A corrected concentration Px of the first allele is calculated based on a number of reactions positive for the first allele, where Px is corrected for an expected statistical distribution of the first allele in the plurality of reactions. A second allele is detected in the reactions, where the second allele is specific to the fetus. A corrected concentration Py of the second allele is calculated based on a number of reactions positive for the second allele. Py is corrected for an expected statistical distribution of the second allele in the plurality of reactions. The fetal percentage Pf is then calculated using $[(2Py)/(Px+Py)]$.

Other embodiments are directed to systems, and computer readable media associated with methods described herein.

A better understanding of the nature and advantages of the present invention may be gained with reference to the following detailed description and the accompanying drawings.

BRIEF DESCRIPTION OF THE DRAWINGS

FIG. 7 is a table 700 showing a dosage imbalance between the target and the reference loci for deletion and duplication mutations on chromosome X.

FIG. 9 shows a table 900 with clinical information of the seven pregnant women who are carriers of hemophilia mutations.

FIG. 10 is a table 1000 showing oligonucleotide sequences and real-time PCR conditions for the allele-discriminative assays (SEQ ID NO: 1-36).

FIG. 11 is a table 1100 showing fetal genotyping for rs6528633 in maternal plasma by digital RMD.

FIG. 12 shows the validation of digital RMD assays with artificial DNA mixtures.

FIG. 13 is a table 1300 showing non-invasive detection of fetal hemophilia mutations in maternal plasma by digital RMD.

FIG. 15 shows digital RMD result for maternal plasma samples from normal pregnancies.

DEFINITIONS

Figure 1:
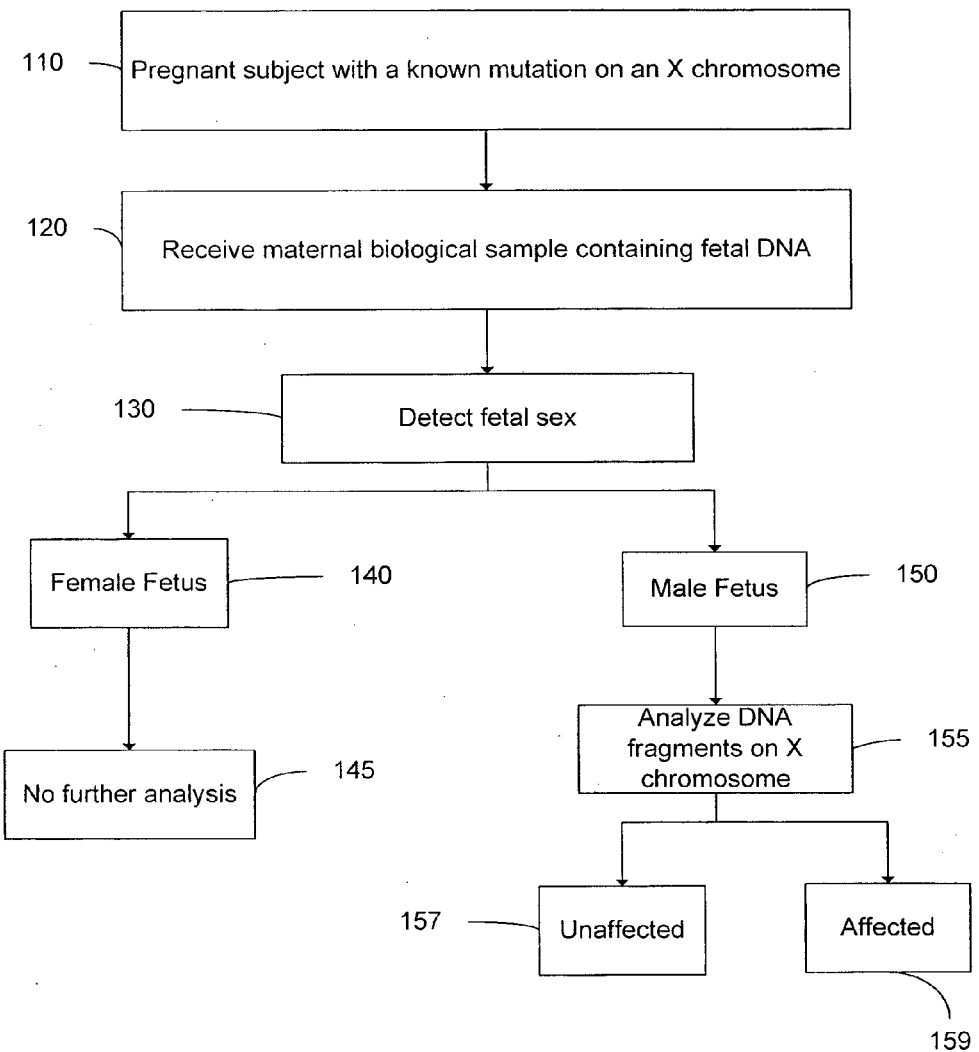
FIG. 1 is a flowchart illustrating a method 100 for analyzing a maternal biological sample to diagnose an X-linked disorder in a fetus according to embodiments of the present invention.

The term "biological sample" as used herein refers to any sample that is taken from a subject (e.g., a human, such as a pregnant woman) and contains one or more nucleic acid molecule(s) of interest.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol.*

Cell. Probes 8:91-98 (1994)). The term nucleic acid is used interchangeably with gene, cDNA, mRNA, small noncoding RNA, micro RNA (miRNA), Piwi-interacting RNA, and short hairpin RNA (shRNA) encoded by a gene or locus.

The term "gene" means the segment of DNA involved in producing a polypeptide chain. It may include regions preceding and following the coding region (leader and trailer) as well as intervening sequences (introns) between individual coding segments (exons).

The term "reaction" as used herein refers to any process involving a chemical, enzymatic, or physical action that is indicative of the presence or absence of a particular polynucleotide sequence of interest. An example of a "reaction" is an amplification reaction such as a polymerase chain reaction (PCR). Another example of a "reaction" is a sequencing reaction, either by synthesis, ligation, hybridization or degradation. An "informative reaction" is one that indicates the presence of one or more particular polynucleotide sequence of interest, and in one case where only one sequence of interest is present. The term "well" as used herein refers to a reaction at a predetermined location within a confined structure, e.g., a well-shaped vial, cell, chamber in a PCR array, a droplet in an emulsion, a particle, a nanopore or an area on a surface.

The term "overrepresented nucleic acid sequence" as used herein refers to the nucleic acid sequence among two sequences of interest (e.g., a clinically relevant sequence and a background sequence) that is in more abundance than the other sequence in a biological sample.

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "quantitative data" as used herein means data that are obtained from one or more reactions and that provide one or more numerical values. For example, the number of wells that show a fluorescent marker for a particular sequence would be quantitative data.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

As used herein, the term "locus" or its plural form "loci" is a location or address of any length of nucleotides (or base pairs) which has a variation across genomes. The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of organisms typically includes multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. As used herein, the term "polymorphism" refers to any inter-individual variation in the human genome, regardless of its frequency. Examples of such variations include, but are not limited to, single nucleotide polymorphisms, simple tandem repeat polymorphisms, insertion-deletion polymorphisms, mutations (which may be disease causing) and copy number variations.

The term "cutoff value" as used herein means a numerical value whose value is used to arbitrate between two or more states (e.g. diseased and non-diseased) of classification for a biological sample. For example, if a parameter is greater than the cutoff value, a first classification of the quantitative data is made (e.g. diseased state); or if the parameter is less than the cutoff value, a different classification of the quantitative data is made (e.g. non-diseased state).

The term "imbalance" as used herein means any significant deviation as defined by at least one cutoff value in a quantity of the clinically relevant nucleic acid sequence from a reference quantity. For example, the reference quantity could be a ratio of 3/5, and thus an imbalance would occur if the measured ratio is 1:1.

The term "sequenced tag" as used herein refers to a string of nucleotides sequenced from any part or all of a nucleic acid molecule. For example, a sequenced tag may be a short string of nucleotides sequenced from a nucleic acid fragment, a short string of nucleotides at both ends of a nucleic acid fragment, or the sequencing of the entire nucleic acid fragment that exists in the biological sample. A nucleic acid fragment is any part of a larger nucleic acid molecule. A fragment (e.g. a gene) may exist separately (i.e. not connected) to the other parts of the larger nucleic acid molecule.

DETAILED DESCRIPTION

Current prenatal diagnostic methods for sex-linked diseases are typically invasive and pose a risk to the fetus. Cell-free fetal DNA analysis in maternal plasma provides a noninvasive means of assessing fetal sex in such pregnancies. However, the disease status of male fetuses remains unknown if mutation-specific confirmatory analysis is not performed. Here we have developed a noninvasive tests to diagnose if the fetus has inherited a causative mutation for sex-linked disease from its mother. One strategy is based on a relative mutation dosage (RMD) approach which we have previously established for determining the mutational status of fetuses for autosomal disease mutations. The RMD method is used to deduce if a fetus has inherited a sex-linked mutation on chromosome X by detecting if the concentration of the mutant or wild-type allele is overrepresented in the plasma of heterozygous women carrying male fetuses.

Embodiments provide the application of the RMD approach in prenatal diagnosis of X-linked disorders, e.g., hemophilia. A difference between the RMD analyses for autosomal diseases and X-linked diseases is that for the former there are three possible fetal genotypes (i.e. homozygous normal, homozygous mutant, and heterozygous) while for the latter there are only two possible fetal genotypes. In the context of X-linked diseases, a male fetus possesses only one chromosome X and thus it would be of either mutant or wild-type genotype. The two outcomes for X-linked diseases, as compared with the three outcomes for autosomal diseases, can make the RMD approach more robust for X-linked diseases for a given degree of analytical precision. Embodiments can also be used for other sex-linked diseases, including but not limited to Duchenne muscular dystrophy, X-linked adrenoleukodystrophy, Becker muscular dystrophy, choroideremia, Hunter syndrome, Lesch Nyhan syndrome, Norrie's syndrome and ornithine transcarbamylase deficiency.

We illustrate the concept using hemophilia, a X-linked bleeding disorder, as an example. We correctly detected fetal genotypes for hemophilia mutations in all of the 12 studied maternal plasma samples obtained from pregnancies at-risk of hemophilia (a sex-linked disease) from as early as the 11$^{th}$ week of gestation. This development would make the decision to undertake prenatal testing less traumatic and safer for at-risk families.

I. Determining Sex-Linked Mutation

FIG. 1 is a flowchart illustrating a method 100 for analyzing a maternal biological sample to diagnose an X-linked disorder in a fetus according to embodiments of the present invention. Method 100 is noninvasive and can use DNA circulating in the maternal biological sample.

In step 110, a pregnant subject with a known mutation on an X chromosome is identified. The mutation may be of any type as described herein, such as hemophilia. The mutation may be determined in a variety of ways, such as DNA sequencing, Southern blot analysis, PCR (including allele-specific PCR), melting curve analysis, etc. The mutation is such that only one of the X chromosomes of the pregnant subject has the mutation, i.e., the pregnant subject is heterozygous at a locus associated with the mutation. Embodiments can also be applied for the noninvasive prenatal diagnosis of other sex-linked disorders involving point mutations or sequence deletion, duplication or inversion, for examples, choroideremia and Norrie's syndrome.

In step 120, a biological sample of the pregnant subject is received. The sample may be any biological sample that contains fetal nucleic acids, such as plasma, urine, serum, and saliva. For example, maternal plasma sample can be collected from a pregnant carrier receiving obstetric care.

In step 130, the sex of the fetus is determined. The sex can be determined by detecting X and Y chromosomes. Through the detection of chromosome Y DNA sequences in maternal plasma, male fetuses could be identified with an accuracy of greater than 97% from the 7$^{th}$ week of gestation onwards. Unnecessary invasive testing could be avoided for female fetuses, as they are either unaffected or are disease carriers.

In step 140, the fetus is determined to be female, and then no further analysis is performed at step 145. Female fetuses are affected as carriers, except rare scenarios like skewed X-inactivation.

In step 150, the fetus is determined to be male, and then in step 155, DNA fragments on the X chromosome are analyzed. In one embodiment, a fetal mutation detection is performed by a relative mutation dosage (RMD) technique, which is described in more detail below. In another embodiment, a fetal mutation of a deletion or amplification is detected by comparing an amount of alleles at a target region (which includes the mutation in the mother) to an amount of alleles at a reference region, which is normal in the mother.

In step 157, a determination that the fetus did not inherit the mutated X chromosome of the maternal subject can be made. In step 159, a determination that the fetus did inherit the mutated X chromosome of the maternal subject can be made. The classification could be confirmed, if necessary, by a second maternal plasma sample taken at a later stage of pregnancy when fetal DNA percentages are higher (Lun F M F et al., *Clin Chem.*, 54:1664-1672 (2008)), allowing for more robust testing.

II. Classification Between Normal and Mutant

The analysis in step 155 of method 100 analyzes DNA fragments in the maternal sample. As the maternal sample also contains fetal DNA, a genotype of the X chromosome of the male fetus can be determined. For any mutation on chromosome X, there is always an allelic imbalance between the concentrations of the mutant and the wild-type alleles in the plasma of heterozygous women carrying male fetuses. The overrepresented allele is the one inherited by the fetus. In one embodiment, the genotype of the fetus can be determined by the RMD technique, which can include comparing a number of mutant alleles to a number of normal alleles in the maternal sample.

Figure 2:
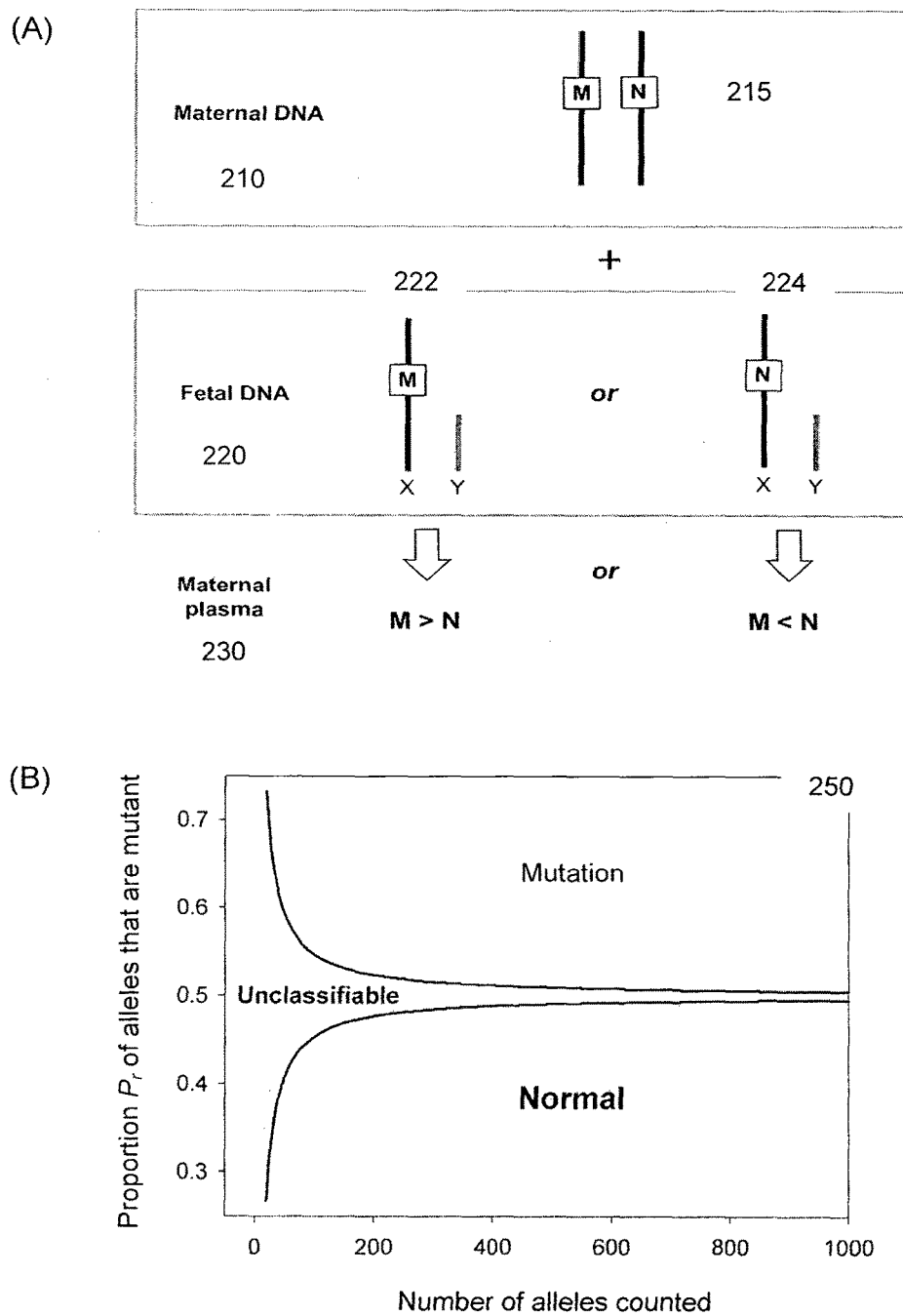
FIG. 2A illustrates the two possibilities of the fetus inheriting the mutant allele or the normal allele.
FIG. 2B shows a plot 250 of cutoff values for classifying a sample as obtained using sequential probability ratio test (SPRT) according to embodiments of the present invention

FIG. 2A illustrates the two possibilities of the fetus inheriting the mutant allele or the normal allele. The maternal DNA 210 is shown for a particular locus on the X chromosomes. The locus 215 is heterozygous with one allele being normal N (wild type) and the other allele being mutant M. The mutation can be of various types, such as a different sequence, a deletion, an insertion, and an inversion. Each of these mutations can be identified as a different allele than the normal allele at locus 215.

The fetal DNA 220 is shown with the two possibilities. Since the male fetus has only one X chromosome, only one of the X chromosomes of maternal DNA 210 will be inherited by the male fetus. Possibility 222 shows the male fetus inheriting the mutant allele M. Possibility 224 shows the male fetus inheriting the normal allele N. The Y chromosome, which is smaller than the X chromosome, is also shown for each possibility.

The maternal sample (e.g. plasma) 230 will have a different proportion of mutant alleles to normal alleles depending on whether the fetus inherits the mutant or normal alleles. For possibility 222, the maternal sample will have more mutant alleles M since the male fetus had inherited the mutant allele M. This is because the fetal DNA would only contribute the mutant allele M, while the maternal DNA would contribute roughly equal parts of mutant allele M and normal allele N when a statistically significant amount of DNA is analyzed. For possibility 224, the maternal sample will have more normal alleles N since the male fetus had inherited the normal allele N.

The number of DNA fragments showing the normal and mutant alleles can be counted in various ways, such as digital PCR, sequencing (including Sanger sequencing, massively parallel sequencing and single molecule sequencing), and other methods that would allow the analysis of single DNA molecules or amplified groups of DNA molecules (e.g. clusters on a solid surface). Once the number of N and M alleles are counted, various techniques can be used to perform a classification, such as affected or unaffected (e.g. a diagnosis of whether the fetus has hemophilia or is normal). For instance, a parameter (e.g. a ratio or a difference) can be determined from the number of N and M alleles, and the parameter can be compared against one or more cutoff values. The cutoff value(s) can be obtained through various statistical techniques, such as sequential probability ratio test (SPRT) (Zhou W, Galizia G, Lieto E, et al., *Nat Biotechnol.*, 19:78-81 (2001); Zhou W, Goodman S N, Galizia G, et al., *Lancet.*, 359:219-225 (2002)).

FIG. 2B shows a plot 250 of cutoff values for classifying a sample as obtained using SPRT according to embodiments of the present invention. The Y-axis shows the proportion $P_r$ (an example of a parameter) of alleles that are mutant. The X-axis shows the number of alleles for locus 215 that are counted. The two curves correspond to the cutoff values for determining whether the fetus has the mutation (e.g. hemophilia), is normal, or is unclassifiable. Samples with mutant allele proportion ($P_r$) above the upper boundary and below the lower boundary are classified as mutant and wild-type, respectively. Samples with $P_r$ in between the two curves are unclassifiable and require additional digital analysis (e.g., data from additional PCR wells).

The particular cutoff values to use depends on the number of alleles counted. When only a few alleles are counted, there can be a large statistical variation, and thus the cutoff values require extreme values in $P_r$ to confidently classify the sample as mutant or normal. As is described in more detail below, digital PCR may be used (where the Y-axis can be the proportion of positive wells containing the mutant allele and the X-axis can be the number of positive wells). The position of the curves on the Y-axis can change depending on how the parameter is calculated, e.g., the unclassifiable area could be centered at 1.0 if the parameter was the number of N alleles divided by the number of M alleles.

In another implementation, where the mutation is a deletion or amplification, a comparison between a number of fragment at a target region (e.g. locus 215) where one of the maternal X chromosomes has a deletion/amplification and a reference region (not having an amplification or deletion) can be used to identify the deletion/amplification. Such an implementation does not depend on an identification of a heterozygous locus, thus the pregnant subject can be homozygous at the target region. For a deletion, one would expect fewer fragments from the target region than from the reference region. For an amplification, one would expect more fragments from the target region than from the reference region. The cutoff values can also be determined using SPRT or similar techniques.

III. RMD Method

Figure 3:
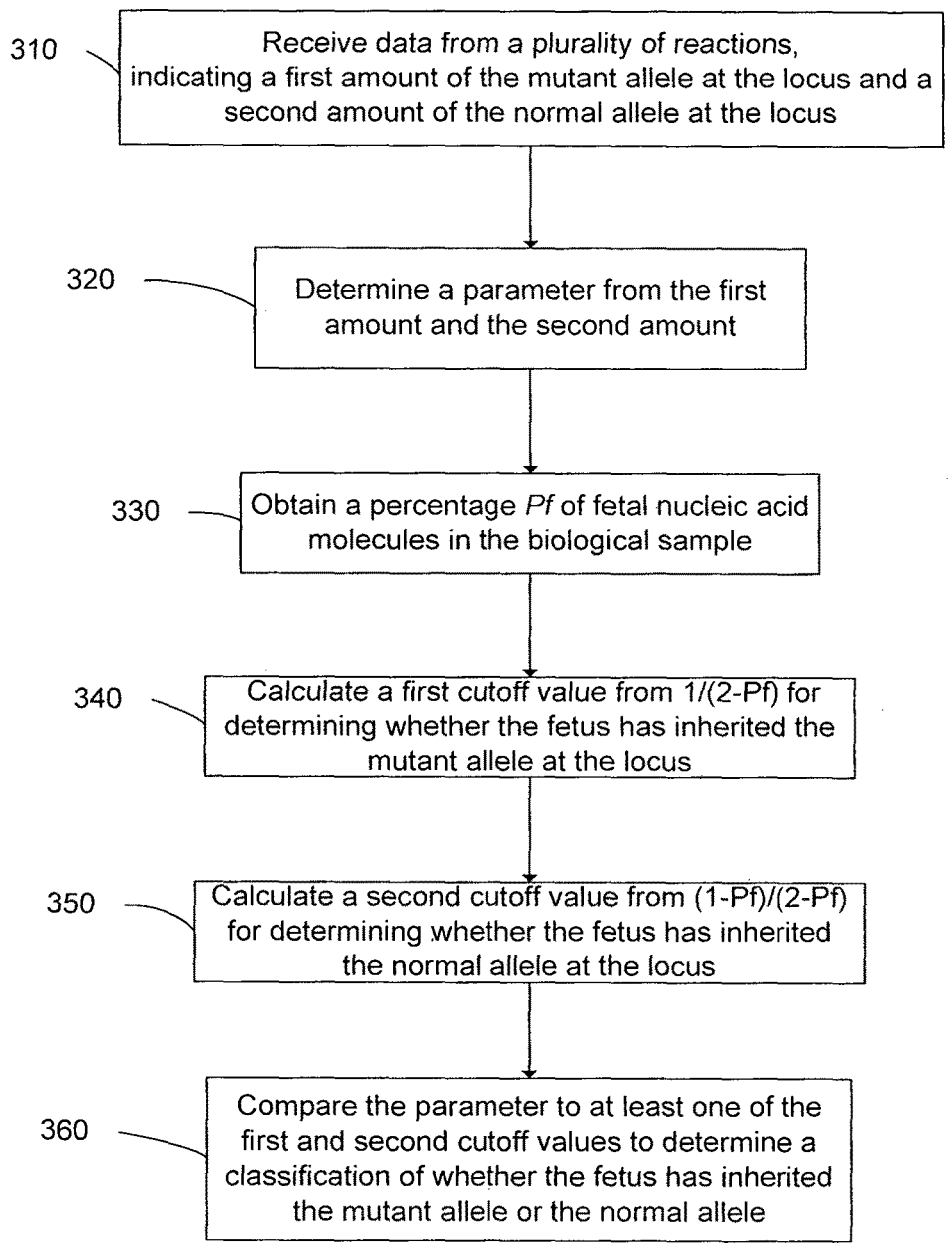
FIG. 3 is a flowchart illustrating a method 300 for determining whether a male fetus of a pregnant female has an X-linked mutation according to embodiments of the present invention.

FIG. 3 is a flowchart illustrating a method 300 for determining whether a male fetus of a pregnant female has an X-linked mutation according to embodiments of the present invention. The pregnant female is heterozygous for a mutant and a normal allele at a locus on the X chromosome. Method 300 uses a relative amount of the mutant and normal allele to make a disease classification.

In step 310, data from a plurality of reactions is received. Each reaction involves one or more nucleic acid molecules from a biological sample, which includes nucleic acid molecules from the pregnant female and from the male fetus. The reactions can be of various types, such as digital PCR reactions in various wells. Other embodiments can use other reactions, such as sequencing reactions (for example by a massively parallel sequencing platform, including but not limited to the Illumina Genome Analyzer, Roche 454, Life Technologies SOLiD, Pacific Biosciences single molecule real-time sequencing or Ion Torrent), primer extension reactions, mass spectrometry, analysis using a nanopore, optical methods or hybridization to a fluorescent or other probe. Thus, the data can include fluorescent signals from digital PCR wells, sequenced tags obtained from sequencing at least a portion of the DNA molecules in the wells, or other data resulting from such reactions.

The data from the reactions includes a first set of quantitative data indicating a first amount of the mutant allele at the locus, and a second set of quantitative data indicating a second amount of the normal allele at the locus. The amount for a particular allele at the locus can be measured in various ways, such as by a total number of wells that are positive for a particular allele, counting the number of sequenced tags that include the particular allele and align to the locus (using a reference genome), and the number of sequenced nucleotides (basepairs) or the accumulated lengths of sequenced nucleotides (basepairs) that include the particular allele and align to the locus.

In step 320, a parameter is determined from the first amount and the second amount. The parameter represents a relative amount between the first and second amounts. The parameter may be, for example, a simple ratio of the first amount to the second amount, or the first amount to the second amount plus the first amount. In one aspect, each amount could be an argument to a function or separate functions, where a ratio may be then taken of these separate functions. One skilled in the art will appreciate the number of different suitable parameters. For example, the parameter can be a ratio of the number of mutant alleles to the total number of mutant and wild-type alleles, denoted by $P_r$, present in a plasma sample.

In step 330, a percentage Pf of fetal nucleic acid molecules in the biological sample is obtained. The percentage Pf provides a measurement of how much fetal DNA is in the maternal sample relative to the maternal DNA. If the percentage Pf is higher, then the overrepresentation of the inherited allele will become larger. The percentage can be expressed as a fraction between 0 and 1, with 1 being 100%.

In step 340, a first cutoff value for determining whether the fetus has inherited the mutant allele at the locus is calculated. The first cutoff value is derived at least from a first proportion of $1/(2-N)$. Depending on how the parameter from step 320 is formulated, the proportion $1/(2-N)$ can be equal to the expected ratio of the first and second amounts if the mutant allele was inherited. The expected value can be input into a statistical function to determine the cutoff. The cutoff value may be determined using many different types of methods, such as SPRT, false discovery, confidence interval, and receiver operating characteristic (ROC) curve analysis.

In step 350, a second cutoff value for determining whether the fetus has inherited the normal allele at the locus is calculated. The second cutoff value is derived at least from a second proportion of $(1-Pf)/(2-Pf)$.

In step 360, the parameter is compared to at least one of the first and second cutoff values to determine a classification of whether the fetus has inherited the mutant allele or the normal allele. As mentioned above, the classifications can include affected (mutation inherited) and unaffected (normal inherited), and also may include unclassified. A probability of accuracy may also be included with the classification, e.g., the accuracy may be determined by how much the parameter exceeds (above or below) a cutoff. In one implementation, the classification may be a score that is to be interpreted at a later date, for example, by a doctor.

The data that indicates an amount of an allele can be from a linked allele. Thus, an allele that is linked to either the mutant or the normal allele can be used instead of the normal and mutant alleles. For example, an allele at a polymorphic site linked to the mutant nucleic acid sequence can be an allele located on the same maternal haplotype as the mutant nucleic acid sequence, where the probability of recombination between the polymorphic site and the mutant nucleic acid sequence is less than a certain value, e.g. 1%. Thus, the polymorphic site can provide the same or similar quantitative data as measuring the mutant allele directly. As another example, an allele at a polymorphic site linked to the normal nucleic acid sequence can be an allele located on the same maternal haplotype as the normal nucleic acid sequence, where the probability of recombination between the polymorphic site and the mutant nucleic acid sequence is less than a certain value, e.g. 1%.

A. Example Using PCR with Plasma

As mentioned above, digital PCR can be used as the method for identifying DNA fragments that include the mutant or normal allele. In digital PCR, a sample is separated into a plurality of compartments (e.g., wells and beads). On average, each compartment contains less than one of any of the two alleles. Thus, a positive well can be counted as a single instance of a fragment containing the allele.

Figure 4:
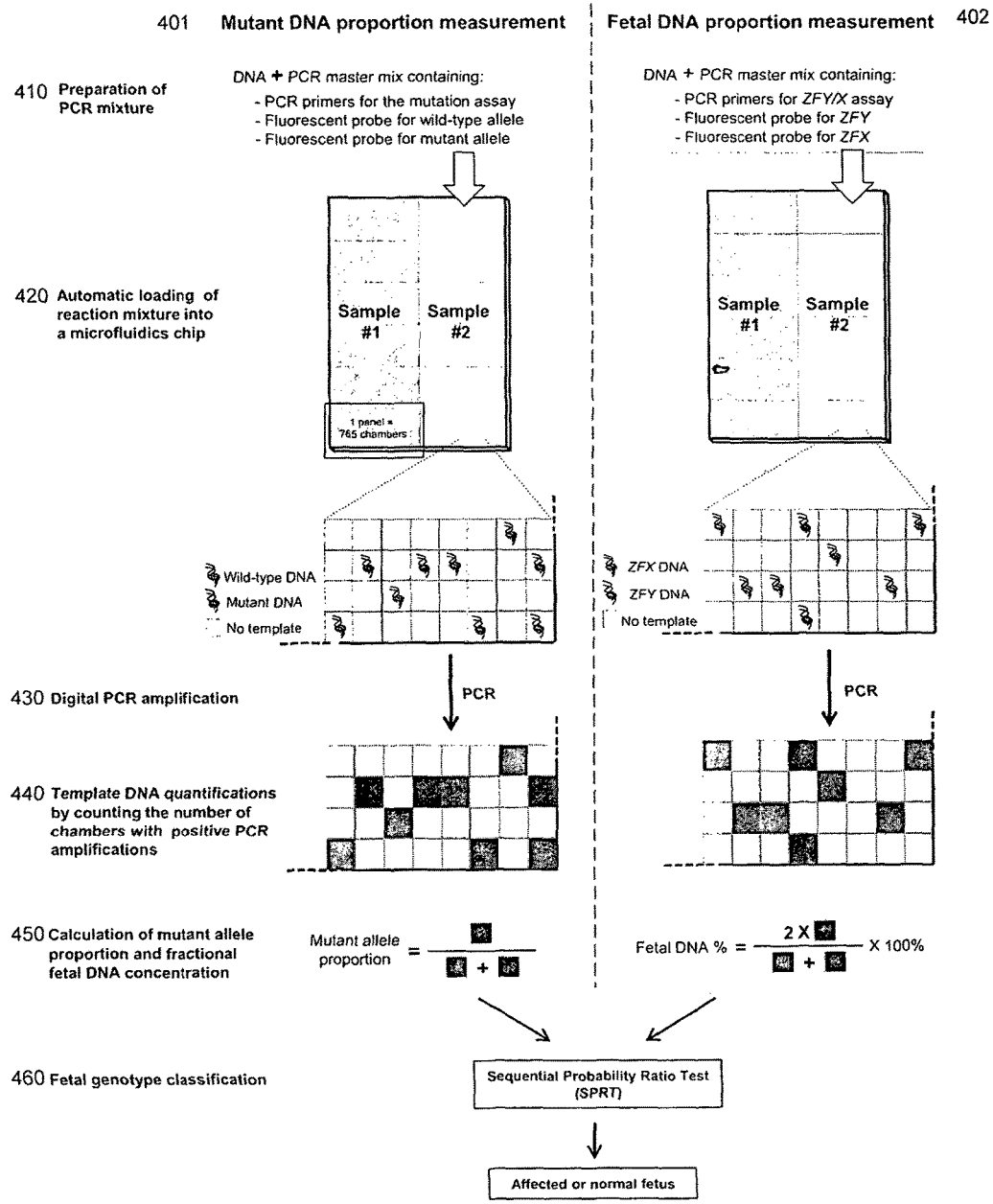
FIG. 4 illustrates a method 400 for determining whether a male fetus has inherited an X-linked mutation according to embodiments of the present invention.

FIG. 4 illustrates a method 400 for determining whether a male fetus has inherited an X-linked mutation according to embodiments of the present invention. Digital PCR is used to determine a mutant allele proportion and the fetal DNA percentage. The fetal DNA percentage is used to determine a cutoff value to which the mutant allele proportion is compared, thereby providing a classification of whether the male fetus has inherited the mutation. As the mutant allele proportion is determined, embodiments can be referred to as the RMD method.

As illustrated, for each maternal plasma DNA sample, both the mutant DNA proportion ($P_r$) and the fetal DNA percentage Pf are determined by digital PCR, although other reactions that can identify certain sequences may be used. Steps for determining $P_r$ is provided on the left (process 401), and steps for determining the fractional fetal DNA concentration Pf are on the right (process 402). As shown, $P_r$ is determined using a real-time PCR assay targeting the mutation carried by the mother, while the fetal DNA percentage Pf is determined using the real-time PCR assay for the homologous ZFY and ZFX gene regions.

In step 410, the PCR mixture is prepared. As shown, the mixtures are different for the two measurements. For the $P_r$ measurement (process 401), the mixture contains PCR primers to amplify a region on the X chromosome that includes the locus to be tested. The mixture also contains a fluorescent probe to identify the existence of a DNA fragment with the wild-type allele, and a fluorescent probe to identify the existence of a DNA fragment with the mutant allele. For the Pf measurement (process 402), the mixture contains primers for the ZFY and ZFX gene regions. The mixture also includes fluorescent probe to identify the existence of a DNA fragment containing a sequence from the ZFX gene, and a fluorescent probe to identify the existence of a DNA fragment containing a sequence from the ZFY gene.

In step 420, the reaction mixtures are loaded into a PCR machine. In one embodiment, the digital PCR is carried out in a microfluidics Digital Array (Fluidigm), which consists of 12 panels with each panel further partitioned into 765 reaction chambers. Each DNA sample (i.e. one for $P_r$ and one for Pf) is analyzed using 6 panels, i.e., 765×6=4590 chambers. The PCR mixture can be first manually added into the sample inlet of each panel. The mixture is next aliquoted into 765 chambers in each panel automatically by an Integrated Microfluidics Circuit Controller (Fluidigm). Each chamber contains a final reaction volume of 6 nL. The cell-free DNA concentration in maternal plasma is typically very low such that there is less than one template molecule per chamber on average. Hence, the distribution of template molecules to the chambers follows the Poisson distribution. For other samples, one may need to dilute the DNA sample before analysis. It will also be obvious to those of skill in the art that the digital PCR can be performed using methods well-known to those of skill in the art, e.g. microfluidics chips, nanoliter PCR microplate systems, emulsion PCR (including the RainDance platform), polony PCR, rolling-circle amplification, primer extension and mass spectrometry.

As shown for the $P_r$ measurement, wells (chambers) containing a DNA fragment with the wild-type allele are shown in blue, and wells containing a DNA fragment with the mutant allele are shown in red. Wells that do not contain a temple DNA molecule (i.e. no allele for which there is a probe) are shown simply as white. Similarly for the Pf measurement, wells containing the ZFX gene are shown in blue, and wells containing the ZFY gene are shown in red.

In step 430, real-time PCR is performed, e.g., on the BioMark System (Fluidigm). Each well is carried through a series of cycles that amplify DNA regions that correspond to the primers in the corresponding mixture. Since most of the chambers contain zero or one template DNA molecule, the amplified products from a well originate from one template DNA molecule.

In step 440, the number of chambers with positive PCR amplifications are counted. For the process 401, the number of chambers that are positive for the wild-type allele can be counted and the number of chambers for the mutant allele can be counted. For process 402, the number of chambers that are positive for the ZFX gene can be counted and the number of chambers for the ZFY gene can be counted. In each process, the number of chambers that are positive for both of the alleles can also be identified. The detection of a positive chamber can be performed in various ways, such as detecting a fluorescent signal (e.g. each allele will emit a different color signal). For example, chambers containing the ZFX gene can emit a blue fluorescent signal, and wells containing the ZFY gene can emit a red fluorescent signal.

In step 450, the mutant DNA proportion ($P_r$) and the fetal DNA percentage Pf are calculated using the corresponding numbers counted in step 440. For example, the mutant allele proportion could be calculated as the number of chambers positive for the mutant allele divided by the total number of positive wells. As other examples, the denominator could be the total number of chambers that are positive only for one allele. Instead of a ratio involving the raw number of counts, the values could be concentrations themselves, effectively dividing the numerator and the denominator by any of the values above. Similar values can be used to calculate the fetal DNA percentage Pf using the equation $[(2Y)/(X+Y)]*100\%$, where Y is the measured amount for the ZFY gene (e.g., count of positive chambers or proportion of positive chambers), and X is the measured amount for the ZFX gene.

Since there was less than one template molecule per reaction well, the actual number of template molecules distributed to each reaction chamber followed the Poisson distribution. Hence, the number of chambers for any allele can be Poisson-corrected using the equation $[-\ln((N-P)/N)]*N$, where N is the total number of reaction chambers analyzed, P is the number of chambers positive for the allele, and ln is the natural logarithm. The Poisson-corrected values can then be used in a similar manner as mentioned above to determine the proportion $P_r$ and the fetal DNA percentage Pf.

In step 460, the mutant DNA proportion ($P_r$) and the fetal DNA percentage Pf are used to perform a classification of whether the male fetus had inherited the mutation or not. As for method 300, cutoff values can be determined from the fetal DNA percentage Pf, e.g., as in steps 340 and 350. The cutoff may also be derived from (which includes equal to) an average reference template concentration ($m_r$), e.g., the experimentally measured percentage of positive chambers for the wild-type allele can be used to determine the cutoff value used in step 460. This strategy can further minimize the amount of testing required before confident classification could be made. This is of particular relevance to plasma nucleic acid analysis where the template amount is often limiting.

B. SPRT

SPRT is a method which allows two probabilistic hypotheses to be compared as data accumulate. In other words, it is a statistical method to classify the results of digital PCR as being suggestive of the skewing towards either the mutant or the normal allele. It has the advantage of minimizing the number of wells to be analyzed to achieve a given statistical power and accuracy.

In an exemplary SPRT analysis, the experimental results would be tested against two alternative hypotheses. The first alternative hypothesis is accepted when the mutant allele is over-represented. The second alternative hypothesis is accepted when the mutant allele is under-represented. The measured $P_r$ would be compared with at least one of the two cutoff values to accept the first or the second alternative hypotheses. If neither hypothesis is accepted, the sample would be marked as unclassified which means that the observed digital PCR result is not sufficient to classify the sample with the desired statistical confidence. More data can be collected to obtain the desired statistical confidence.

A pair of curves, which depend on the amount of data collected, can define the probabilistic boundaries (cutoffs) for accepting or rejecting the hypotheses (Zhou W, Galizia G, Lieto E, et al., *Nat Biotechnol.*, 19:78-81 (2001); Zhou W, Goodman S N, Galizia G, et al., *Lancet.*, 359:219-225 (2002)). The SPRT curves delineated the required $P_r$ (y-axis) for a given total number of positive reactions (x-axis) for classifying a fetal genotype. Hypothesis (i) or (ii) are accepted if the experimental $P_r$ fell above the upper boundary or below the lower boundary, respectively. The equations for calculating the SPRT boundaries can be determined with varying levels of statistical confidence (e.g. adjusted to a threshold likelihood ratio of 8). In one aspect, the cutoff values of the SPRT curves are sample-specific. The cutoff values are dependent on the fractional fetal DNA concentration (fetal DNA percentage) as described above. The cutoff values can also depend on an average reference template concentration per PCR well ($m_r$) for a given set of reactions (Lo Y M D et al., *Proc Natl Acad Sci USA.* 2007; 104:13116-13121 (2007); Lun F M F, Tsui N B Y, Chan K C A, et al., *Proc Natl Acad Sci USA.*, 105:19920-19925 (2008)). The reference template can refer to the allele that showed the lesser positive amplification counts in the sample.

SPRT can offer an advantage that a smaller amount of testing is required for a given level of confidence than other statistical methods. In practical terms, SPRT allows the acceptance or rejection of either of the hypotheses as soon as the required amount of data has been accumulated and thus minimizes unnecessary additional analyses. This feature is of particular relevance to the analysis of plasma nucleic acids which are generally present at low concentrations where the number of available template molecules is limiting. In addition to a strict classification, the classification may also include a percent accuracy. For example, a classification resulting from a comparison with a cutoff value may provide that a sample shows a likelihood of a nucleic acid sequence imbalance with a certain percentage, or equivalently that a determined imbalance is accurate to a certain percentage or other value.

For embodiments using SPRT, one may use the equations for calculating the upper and lower boundaries of the SPRT curves from El Karoui at al (El Karoui N, Zhou W, Whittemore A S, *Stat Med.* 25:3124-3133 (2006)). Furthermore, the level of statistical confidence preferred for accepting the first or second hypothesis could be varied through adjusting the threshold likelihood ratio in the equations. A threshold likelihood ratio of 8 has been shown to provide satisfactory performance to discriminate samples with and without allelic imbalance in the context of cancer detection. Thus, in one embodiment, the equations for calculating the upper and lower boundaries of the SPRT curves are:

Upper boundary=$[(\ln 8)/N - \ln \delta]/\ln \gamma$

Lower boundary=$[(\ln \frac{1}{8})/N - \ln \delta]/\ln \gamma$ where, $$\delta = (1-\theta_1)/(1-\theta_2), \gamma = \frac{\theta_1(1-\theta_2)}{\theta_2(1-\theta_1)},$$

ln is a mathematical symbol representing the natural logarithm, i.e. $\log_e$, N=total number of molecules (i.e. the sum of mutant and normal molecules analyzed), $\theta_1$=proportion of mutant molecules to the total number of mutant and normal molecules if the first alternative hypothesis is true (i.e., the fetus has inherited the mutant allele); and $\theta_2$=proportion of mutant molecules to the total number of mutant and wild-type molecules if the second alternative hypothesis is true (i.e., the fetus has inherited the normal allele).

For the determination of $\theta_1$ for accepting the first alternative hypothesis, the sample is assumed to be obtained from a pregnant woman carrying a male fetus which has inherited the mutant (M) allele. $\theta_1$ is determined to be $1/(2-Pf)$, where Pf is the percentage of fetal DNA in the sample. Pf can be corrected for a statistical distribution, such as the Poisson distribution, as is described herein.

For the determination of $\theta_2$ for accepting the second alternative hypothesis, the sample is assumed to be obtained from a pregnant woman carrying a male fetus which has inherited the normal (N) allele. $\theta_2$ is determined to be $(1-Pf)/(2-Pf)$.

After an experimental determination of the numbers of mutant and wild-type molecules, the proportion of mutant molecules to the total number of mutant and wild-type molecules (Pr) can be calculated. The value of Pr can then be compared with the cutoff values to determine if the mutant or the wild-type alleles are overrepresented in the maternal plasma.

C. Poisson Correction of Cutoff Values

In one embodiment using digital PCR, the average concentration per well (reaction or reaction mixture) is determined, and the expected number of wells showing that sequence may be calculated. This amount may be expressed as a percentage, a fractional value, or an integer value. In one implementation, a Poisson distribution is assumed for the distribution of the normal (N) allele, or the mutant allele, among the reaction mixtures of the wells of the measurement procedure, such as digital PCR. In other implementations, other distribution functions are used, such as a binomial distribution.

The Poisson equation is:

$$P(n) = \frac{m^n e^{-m}}{n!}$$

where, n=number of template molecules per well; P(n)=probability of n template molecules in a particular well; and m=average number of template molecules in one well in a particular digital PCR experiment. Accordingly, the probability of any well not containing any molecule of the normal allele at an average normal-allele concentration of 0.5 would be:

$$P(0) = \frac{0.5^0 - e^{-0.5}}{0!} = e^{-0.5} = 0.6065.$$

Hence, the probability of any well containing at least one molecule of the normal allele would be: 1−0.6065=0.3935. Therefore, ~39% of the wells would be expected to contain at least one molecule of the normal allele. In one embodiment, P(0) for mutant or wild-type can be determined from an experimentally derived proportion of negative wells (e.g. using digital PCR). P(0) can then be used to calculate the average number of molecules per well (m). The parameter can then be calculated from the average number of molecules per well, e.g., mutant average divided by the sum of the averages for the mutant and normal alleles. Given this relationship between the number of positive wells and the number of molecules, an alternative is to correct the number of positive wells to provide the number of molecules (as described above via equation [−ln((N−P)/N)]*N, where N is the total number of reaction chambers analyzed and P is the number of chambers positive for the allele).

The measurement of $m_r$ may be performed through a variety of mechanisms as known or will be known to one skilled in the art. In one embodiment, the value of $m_r$ is determined during the experimental process of digital PCR analysis. As the relationship between the value of $m_r$ and the total number of wells being positive for the reference allele can be governed by a distribution (e.g. the Poisson distribution), $m_r$ can be calculated from the number of wells being positive for the reference allele using this formula:

$m_r$=−ln(1−proportion of wells being positive for the reference allele)

This approach provides a direct and precise estimation of $m_r$ in the DNA sample used for the digital PCR experiment.

This method may be used to achieve a desired concentration. For example, the extracted nucleic acids of a sample may be diluted to a specific concentration, such as one template molecule per reaction well. In an embodiment using the Poisson distribution, the expected proportion of wells with no template may be calculated as $e^{-m}$, where m is the average concentration of template molecules per well. For example, at an average concentration of one template molecule per well, the expected proportion of wells with no template molecule is given by $e^{-1}$, i.e., 0.37 (37%). The remaining 63% of wells will contain one or more template molecules. Typically, the number of positive wells in a digital PCR run would then be counted. The definition of informative wells and the manner by which the digital PCR data are interpreted depends on the application.

In other embodiments, the average concentration per well, $m_r$, is measured by another quantification method, for example, quantitative real-time PCR, semi-quantitative competitive PCR, and real-competitive PCR using mass spectrometric methods.

In one implementation, the proportion of the mutant allele to the normal allele can be calculated using corrected concentrations. The concentration m for each allele can be calculated as described above. The concentration for each allele can then be determined, and a proportion Pr of the concentrations can be used as the experimentally derived and distribution-corrected proportion to compare to the expected proportion for each hypothesis (e.g. mutant or wild-type inheritance). For example, the experimentally determined Pr of a tested sample can be calculated using the equation: (concentration of mutant allele)/(concentration of mutant+wild-type alleles). In another implementation, the proportion of the number of wells for each allele is used. The expected proportion (cutoff value) can also be corrected based on a statistical distribution.

D. Illustration

Figure 5:
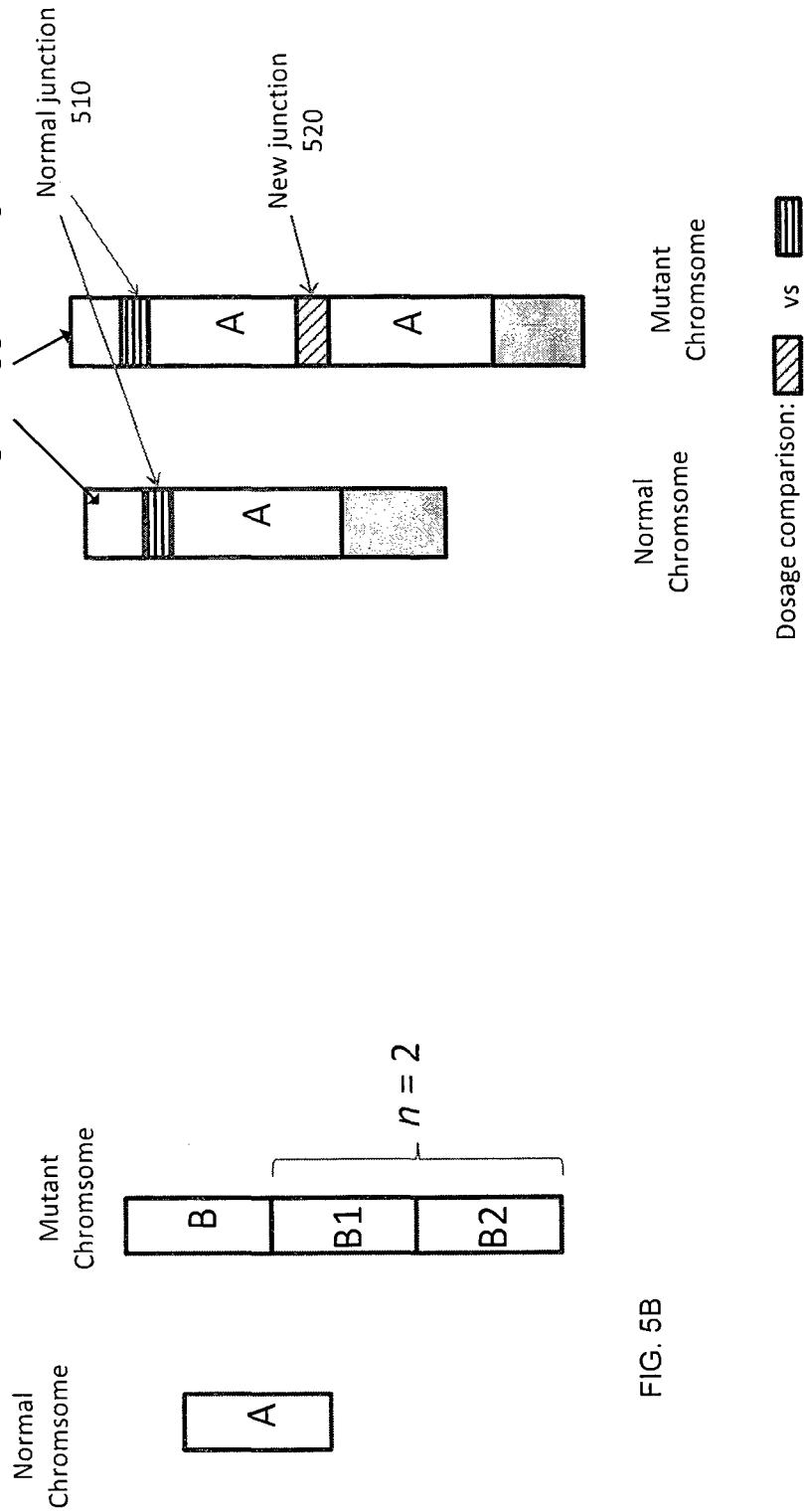
FIG. 5A shows a table 500 illustrating a dosage imbalance between mutant and wild-type alleles for mutations on chromosome X.
FIG. 5B illustrates a first scenario for detecting an amplification when the pregnant subject is heterozygous at the locus of interest.
FIG. 5C illustrates a second scenario for detecting an amplification when the pregnant subject is homozygous at the locus of interest.

FIG. 5A shows a table 500 illustrating a dosage imbalance between mutant and wild-type alleles for mutations on chromosome X according to embodiments of the present invention. To illustrate the calculation, a maternal plasma sample containing a total of 100 genomic equivalents (GE) of DNA with 10% fetal DNA was used. For the maternal genome, one GE contains two copies of the alleles, i.e., one copy each of the M and the N allele. This provides 90 copies each of the mutant and normal alleles. For the fetal genome, one GE contains one copy of the X-linked allele, i.e., one copy of either the mutant (M) or the normal (N) allele. This provides 0 or 10 copies of each allele depending on which allele is inherited by the fetus.

In table 500, the upper row corresponds to the fetus inheriting the normal allele, and thus the ratio of mutant to normal alleles is less than 1. In the lower row, the fetus inherited the mutant allele, and thus the ratio of mutant to normal alleles is greater than 1.

E. Deletions, Amplifications, Insertions, and Inversions

Methods 300 and 400 can be applied in additional situations besides a standard SNP. Embodiment can be further applied to noninvasive detection of fetal mutations involving deletion, amplification (e.g. duplication), insertion, and inversion, e.g., of a large DNA segment. Examples of such mutations are relevant to X-linked diseases such as Duchenne muscular dystrophy, Becker muscular dystrophy and ornithine transcarbamylase deficiency. The approach is to detect the mutant allele by targeting the junctions of the rejoining sequences of the deletion, between the amplified (e.g. duplicated) DNA segments, or between the inverted and the adjacent normal DNA segments. The fetal genotype could then be deduced by the dosage imbalance between the normal and the mutant alleles with the methods described herein.

FIG. 5B illustrates a first scenario for detecting an amplification when the pregnant subject is heterozygous at the locus of interest. For amplifications on a first chromosome, where the amplified allele B is different than the non-amplified allele A, there will be different junctions for the various copies B1 and B2 of the amplified allele B. This is because the amplified copies B1 and B2 will be at different locations on the first chromosome. If one of the junctions is unique (e.g., the junction at the start of B or at the end of B2 is unique, while the junctions between B-B1 and B1-B2 are the same), the unique junction can be used as the mutant allele for comparison to the normal allele on the other chromosome. In this manner, the cutoff values can be derived in the same manner as in steps 340 and 350. Alternatively, all of the instances of the amplified allele B (i.e. is B, B1, and B2) can be used, regardless of location in the first chromosome. In such an embodiment, $\theta_1$=(1+n)/(2+n−Pf), and $\theta_2$=[(1+n)(1−Pf)]/[2+n−Pf(1+n)], where n is the number of additional copies (n=2 as shown), n is an integer equal to or greater than zero. These formulas can also be written as $\theta_1$=k/(1+k−Pf) and $\theta_2$=[k(1−Pf)]/[1+k− kPf)], where k is the number of copies of the mutant allele (which can be a newly formed junction) on the mutant chromosome, where k is an integer equal to or greater than one.

Junctions can also be used in a similar manner for RMD analysis for mutations on autosomes, but the values of $\theta_1$ and $\theta_2$ would need to be adjusted. For example, if the fetus inherited the amplification mutation, the sample would have the same ratio as the mother, assuming the chromosome inherited from the father is the normal chromosome. In this scenario, the value of $\theta_1$ would be k/(k+1), where k is the number of additional junctions created by the amplification mutation, and the additional junction is used as the mutant allele (thus for a duplication or a deletion, there is one mutant allele and for a triple amplification there are two mutant alleles, and so on). If the fetus inherited the normal chromosome from the mother, then the value of $\theta_2$ would be k(1−Pf)/[k+1+(1−k)Pf].

FIG. 5C illustrates a second scenario for detecting an amplification when the pregnant subject is homozygous at the locus of interest. When the amplified allele and the non-amplified allele are the same (A as shown), two junctions 510 will be the same (for the two alleles at the normal location), and the additional (new) junction(s) 520 of the additional copies of the allele will be different, since these additional alleles will be at a different genomic location. The additional junctions can be used as the mutant allele, and the normal junction 510 can be used as the normal allele. One can use just one of the additional junctions 520 for the additional allele(s) (there would be only one for a duplication). In such an embodiment, $\theta_1 = 1/(3-Pf)$; and $\theta_2 = (1-Pf)/(3-2Pf)$. Note that the amount of additional copies is not used in such formulas since just one additional junction is used.

If there are more than one additional copy of A, the additional junction that is used should be chosen to be unique (e.g. the junction after the last amplified copy of A). Or, one could sum all (or some number more than 1) of the additional junctions and compare to the junctions of the two alleles at the normal location. In such an embodiment, $\theta_1 = n/(n+2-Pf)$; and $\theta_2 = n(1-Pf)/[n+2-Pf(n+1)]$, where n is the number of new junctions 520 that are used. Note that the amount of additional copies is used in such formulas since just more than one additional junction is used. Junctions can also be used in a similar manner for RMD analysis for mutations on autosomes, but the values of $\theta_1$ and $\theta_2$ would need to be adjusted. For example, if the fetus inherited the amplification mutation (amplification), the sample would have the same ratio (e.g., 1:2 for a duplication) as the mother, assuming the chromosome inherited from the father does not have the mutation. In this scenario, the value of $\theta_1$ would be n/(n+2), where n is the number of additional junctions created by the amplification mutation. If the fetus inherited the normal chromosome from the mother, then the value $\theta_2$ would be n(1−Pf)/(n+2−nPf). Another approach for detecting deletions and amplifications is described below.

IV. Target Region Vs Reference Region

In the RMD method described above, different junctions can be used as the alleles when the mutation is a deletion, amplification, insertions, or inversion. Another approach, which is applicable to deletion and amplification (e.g. duplication) mutations, is to compare the amount of molecules arising from the target region (i.e. the region that is deleted or amplified) to the amount of molecules arising from a reference region. Any genomic locus on chromosome X not affected by the deletion (or amplification) can be used as a reference locus/region, for example, the ZFX gene if it is not deleted or amplified.

The ratio (R) of the number of molecules from the target region to the number of molecules from the reference region (or some other parameter representing a relative amount) can be used to determine whether the mutation is inherited. In a non-pregnant woman who is carrying the deletion mutation, the expected value of R would be 0.5 because only half of the X chromosomes (those carrying the normal allele) would contribute to the amount of target molecules in the plasma. When a woman carrying this deletion mutation is pregnant with a male fetus, the expected value of R would deviate from 0.5 due to the contribution of the DNA from the one extra X chromosome from the male fetus. The expected deviation of R would depend on whether the mutation is a deletion or an amplification.

Figure 6:
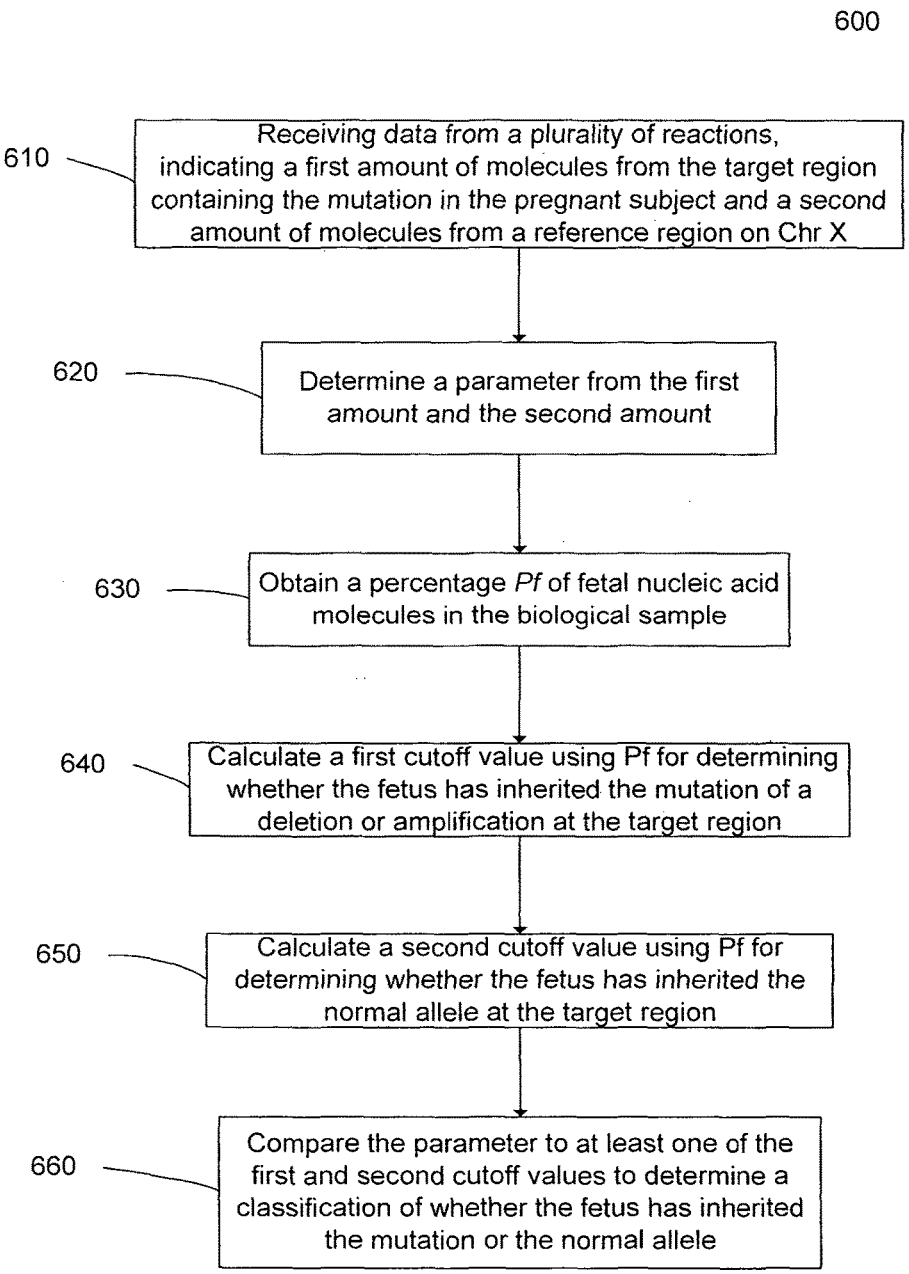
FIG. 6 is a flowchart illustrating a method 600 for determining whether a male fetus of a pregnant female has an X-linked mutation.

FIG. 6 is a flowchart illustrating a method 600 for determining whether a male fetus of a pregnant female has an X-linked mutation. The pregnant female is heterozygous for a mutation and a normal allele at a target region on the X chromosome. The mutation is a deletion or an amplification of the target region.

In step 610, data from a plurality of reactions is received. The data may be of the same type as received in step 310 of method 300. Each reaction involves one or more nucleic acid molecules from a biological sample, which includes nucleic acid molecules from the pregnant female and from the male fetus. The data includes a first set of quantitative data indicating a first amount of the nucleic acid molecules that are from the target region, and a second set of quantitative data indicating a second amount of the nucleic acid molecules that are from a reference region on the X chromosome. The amounts may be computed in various ways, e.g., as described above for step 310.

In step 620, a parameter is determined from the first amount and the second amount. The parameter represents a relative amount between the first and second amounts. In one embodiment, the parameter is a ratio T of the first amount to the second amount. Other embodiments can use parameters as described herein, such the first amount divided by a sum of the first amount and the second amount.

In step 630, a percentage Pf of fetal nucleic acid molecules in the biological sample is obtained. The percentage Pf can be calculated as described herein. The percentage Pf can also be determined from a distribution corrected (e.g. Poisson-corrected) values for counting fetal specific molecules.

In step 640, a first cutoff value for determining whether the fetus has inherited the mutation is calculated. The first cutoff value is dependent on the percentage Pf. The specific equations for calculating the first cutoff value depends on whether the mutation is a deletion or an amplification.

In step 650, a second cutoff value for determining whether the fetus has inherited the normal allele is calculated. The second cutoff value is dependent on the percentage Pf. The specific equations for calculating the first cutoff value depends on whether the mutation is a deletion or an amplification.

In step 660, the parameter is compared to at least one of the first and second cutoff values to determine a classification of whether the fetus has inherited the mutant or the normal allele. The classifications can be of the same type as step 360, such as affected, unaffected, or unclassified (or a raw score).

FIG. 7 is a table 700 showing a dosage imbalance between the target and the reference loci for deletion and duplication mutations on chromosome X. Table 700 illustrates the calculation of the degree of allelic imbalance. An increase or decrease of R when compared with R of a non-pregnant woman carrying the same deletion mutation would indicate a normal or affected fetus, respectively. Conversely, in a non-pregnant woman who is carrying the segmental amplification, such as a duplication as shown in table 700, the expected value of R would be 1.5 due to the contribution of a doubled dose of target molecules from the mutant allele. When a woman carrying this duplication mutation is pregnant, an increase or decrease of R when compared with R of a non-pregnant woman carrying the same duplication mutation would indicate an affected or normal fetus, respectively.

The degree of increase or decrease of R in each scenario is dependent on the fractional fetal DNA concentration (Pf) in a sample. In one embodiment, SPRT analysis can be used to determine if R is statistically significantly increased or decreased compared to the non-pregnant women carrying the same mutation. The equations for calculating the upper and lower boundaries (cutoff values) of the SPRT can have a similar structure of:

Upper boundary=[(ln 8)/N−ln δ]/ln γ;

Lower boundary=[(ln ⅛)/N−ln δ]/ln γ where $$\delta = (1-\theta_1)/(1-\theta_2); \gamma = \frac{\theta_1(1-\theta_2)}{\theta_2(1-\theta_1)};$$

ln is a mathematical symbol representing the natural logarithm, i.e. $\log_e$; N=total number of mutant and reference molecules;

- $\theta_1$=ratio ($R_1$) of target molecules to the reference molecules if the first alternative hypothesis is true (i.e., $R_1$ is increased when compared with the value of R of a non-pregnant woman carrying the same mutation)
- $\theta_2$=ratio ($R_2$) of target molecules to reference molecules if the second alternative hypothesis is true (i.e., $R_2$ is decreased when compared with the value of R of a non-pregnant woman carrying the same mutation)

$\theta_1$ describes the situation in which the ratio of the amount of target molecules to the amount of reference molecules is increased when compared with the corresponding ratio of a non-pregnant woman carrying the same mutation, e.g., a normal case for a deletion mutation, or a mutant case for a duplication mutation. Similarly, $\theta_2$ can describe the situation in which the ratio of the amount of target molecules to the amount of reference molecules is decreased when compared to the corresponding ratio from a non-pregnant woman carrying the same mutation, e.g., a mutant case for a deletion mutation, or a normal case for a duplication mutation.

In one embodiment, for a deletion mutation, $\theta_1$ is calculated as the sample is assumed to be obtained from a pregnant woman carrying a male fetus that has inherited the normal (N) allele. $\theta_1$ is determined to be 1/(2−Pf). $\theta_2$ is calculated as the sample is assumed to be obtained from a pregnant woman carrying a male fetus that has inherited the mutation (e.g. the chromosome X with the deletion mutation). $\theta_2$ is determined to be (1−Pf)/(2−Pf).

In another embodiment, for duplication mutation, $\theta_1$ is calculated as the sample is assumed to be obtained from a pregnant woman carrying a male fetus that has inherited the mutation (i.e. the chromosome X with the duplication mutation). $\theta_1$ is determined to be (3−Pf)/(2−Pf). $\theta_2$ is calculated as the sample is assumed to be obtained from a pregnant woman carrying a male fetus that has inherited the normal (N) allele. $\theta_2$ is determined to be (3−2×Pf)/(2−Pf). The generalized formulas for any level of amplification is: $\theta_1$ is (n+2−Pf)/(2−Pf), and $\theta_2$ is [n+2−Pf(n+1)]/(2−Pf), where n is the number of additional copies of amplified segments.

V. Determining Fetal Percentage

As mentioned above, probabilities P(n) for certain alleles (e.g. specific to chromosome X and a fetal-specific sequence) can be used to adjust the percentage (Pf) of fetal DNA in the sample. This adjusted Pf can then be used to calculate the cutoffs for determining whether the mutant or the wild-type allele is inherited.

Figure 8:
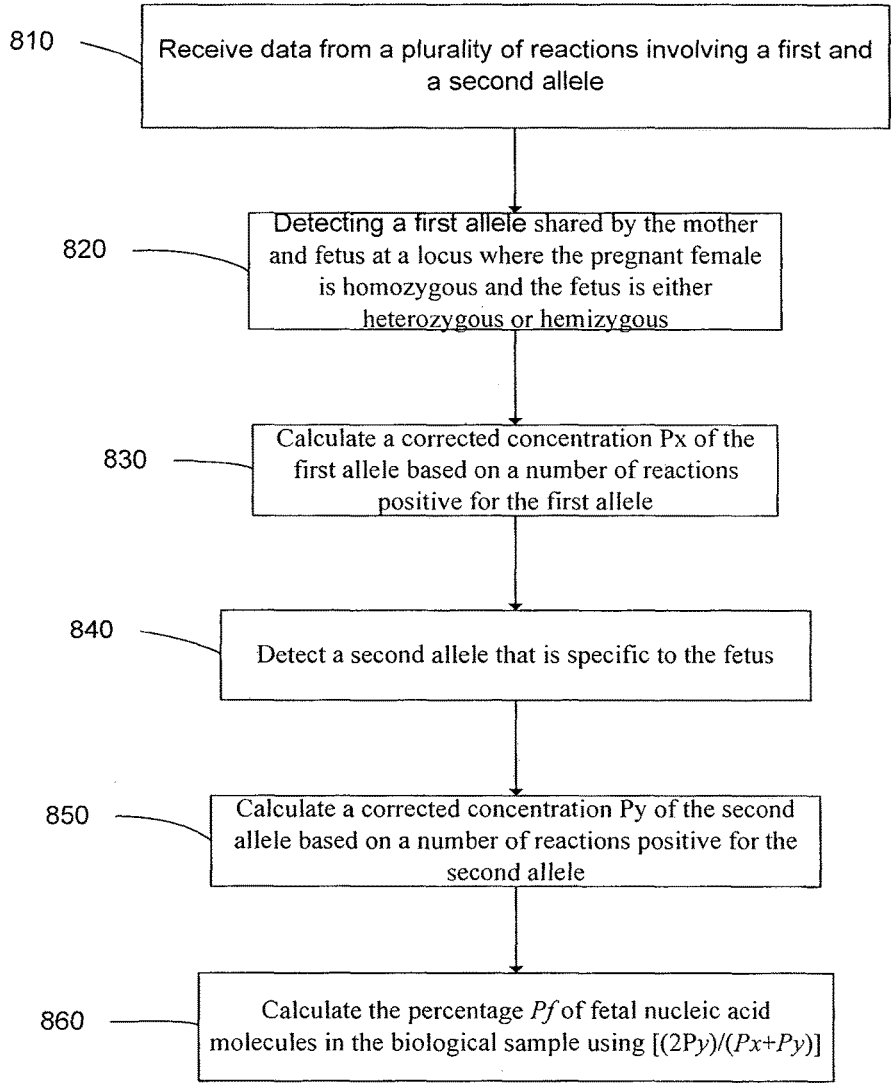
FIG. 8 is a flowchart illustrating a method 800 for obtaining a percentage Pf of fetal nucleic acid molecules in a biological sample from a female pregnant with a fetus according to embodiments of the present invention.

FIG. 8 is a flowchart illustrating a method 800 for obtaining a percentage Pf of fetal nucleic acid molecules in a biological sample from a female pregnant with a fetus according to embodiments of the present invention. The biological sample includes nucleic acid molecules from the pregnant female and from the fetus.

In step 810, data is received from a plurality of reactions. Each reaction involves a plurality of nucleic acid molecules from a biological sample. In one aspect, the reactions may be of any type where a reaction is considered positive for a particular allele if one or more of the alleles are present in the reaction.

In step 820, a first allele is detected in the reactions. The first allele is shared by the mother and fetus at a locus where the pregnant female is homozygous and the fetus is either heterozygous or hemizygous. In one embodiment, the first allele is the X chromosome.

In step 830, a corrected concentration Px of the first allele is calculated based on a number of reactions positive for the first allele. Px is corrected for an expected statistical distribution of the first allele in the plurality of reactions. For example, Px can be corrected based on the Poisson distribution. In one embodiment, a first corrected concentration for a first allele shared by the mother and fetus where the mother is homozygous and the fetus is either heterozygous or hemizygous is calculated, e.g., as [−ln((N−P1)/N)]*N, where N is the total number of reaction chambers analyzed, P1 is the number of chambers positive for the first allele, and ln is the natural logarithm.

In step 840, a second allele that is specific to the fetus is detected. In one embodiment, the second allele is on the Y chromosome, where the fetus is a male fetus. In another embodiment, the fetal-specific allele is a paternally-inherited allele on an autosome. In yet another embodiment, the fetal-specific allele includes a methylation marker specific to the fetus.

In step 850, a corrected concentration Py of the second allele is calculated based on a number of reactions positive for the second allele. Py is corrected for an expected statistical distribution of the second allele in the plurality of reactions. For example, Py can be corrected based on the Poisson distribution. In one embodiment, a second corrected concentration for a fetal-specific allele which the fetus is heterozygous or hemizygous can be calculated as [−ln((N−P2)/N)]*N, where N is the total number of reaction chambers analyzed, P2 is the number of chambers positive for the fetal-specific allele, and ln is the natural logarithm.

In step 860, the percentage Pf of fetal nucleic acid molecules in the biological sample is calculated using [(2Py)/(Px+Py)], which can provide a fractional value. The fetal DNA percentage can be calculated using the equation [(2P2)/(P1+P2)]*100%.

VI. Examples

Seven women who were carriers of hemophilia (three carriers of hemophilia A, four carriers of hemophilia B) and pregnant with male fetuses were recruited from the Royal Free Hospital, London, UK. We also recruited 20 pregnant women (non-carriers of hemophilia) each pregnant with a singleton healthy male fetus. Ten of them were recruited from the Royal Free Hospital, London, UK and the other ten were recruited from the Prince of Wales Hospital, Hong Kong. Clinical information of the cases is shown in table 900 of FIG. 9, which shows clinical information of the seven pregnant women who are carriers of hemophilia mutations.

All women were recruited with informed consent. Ethical approvals were granted by the respective institutional boards. Ten milliliters of peripheral blood samples was collected into EDTA tubes from the pregnant women. For five of the pregnant hemophilia carriers, peripheral blood samples were taken on two occasions during their pregnancies (table 900). None of the pregnant hemophilia carriers in this study had invasive prenatal testing. Fetal sex and hemophilia status were confirmed following delivery. For the ten unaffected pregnant women recruited in Hong Kong, placental tissues were also collected following deliveries.

We centrifuged the blood samples at 1600 g for 10 min at 4° C. The plasma portion was recentrifuged at 16000 g for 10 min at 4° C. Maternal plasma and buffy coat samples were stored at −20° C. until further processing. All samples collected in the UK were processed and stored frozen locally and were shipped on dry ice to Hong Kong. We extracted DNA from maternal plasma with the QIAamp DSP DNA Blood Mini Kit (Qiagen) following the manufacturer's instructions. Buffy coat DNA was extracted using the Illustra DNA Extraction Kit (GE Healthcare) following the manufacturer's protocol.

Genotyping of rs6528633 SNP and Hemophilia Mutations

To assess the feasibility of the RMD approach, we studied a SNP (rs6528633) on chromosome X. This SNP was chosen for illustration purposes and other SNPs can be used. The fetal and maternal SNP genotypes were determined using DNA obtained from the placental and maternal buffy coat samples, respectively. Genotyping was performed using MassARRAY homogenous MassEXTEND (hME) assays (Sequenom) as previously described (Tsui N B Y, Chiu R W K, Ding C, et al., *Clin Chem.*, 51:2358-2362 (2005); Tsui N B Y, Chiu R W K, Ding C, et al., *Clin Chem.*, 51:2358-2362 (2005)). Genomic DNA obtained from the peripheral blood samples of the pregnant hemophilia carriers was used for hemophilia mutation detection. PCRs were performed for all exons covering coding regions, intron/exon boundaries, promoter and 3' UTR. Cycle sequencing was carried out using Big Dye Terminators V1.1 (Applied Biosystems) and analyzed on an Applied Biosystems 3100 Avant Genetic Analyser.

Digital RMD Reactions for Maternal Plasma Analyses

The experimental workflow of digital RMD is illustrated in FIG. 4 according to certain embodiments of the present invention. We measured the fractional fetal DNA concentrations in the maternal plasma samples using the previously described digital ZFY/X assay, which quantified the homologous ZFY and ZFX gene loci located on chromosomes Y and X, respectively (Lun F M F et al., *Clin Chem.*, 54:1664-1672 (2008); Lun F M F, Tsui N B Y, Chan K C A, et al., *Proc Natl Acad Sci USA.*, 105:19920-19925 (2008)). For the rs6528633 SNP, a real-time PCR assay with two allele-specific TaqMan probes (Applied Biosystems) was designed to distinguish the two SNP alleles. For the mutations of the pregnant cases at risk for hemophilia, a real-time PCR assay for allelic discrimination was designed for each mutation. Each assay contained two allele-specific TaqMan probes for the mutant and the wild-type alleles. The primer and probe sequences are listed in table 1000 in FIG. 10, which shows oligonucleotide sequences and real-time PCR conditions for the allele-discriminative assays. In other embodiments, the fractional fetal DNA concentration can be determined by using a sequence that is differentially methylated between the fetal and maternal DNA in maternal plasma (for examples, see Chim S S et al., *Proc Natl Acad Sci USA.*, 102: 14753-14758 (2005); Chan K C A et al., *Clin Chem.*, 52: 2211-2218 (2006)).

We performed digital PCR analyses on the BioMark System (Fluidigm) using the 12.765 Digital Arrays (Fluidigm) (Lun F M F et al., *Clin Chem.*, 54:1664-1672 (2008)). Six of the 12 panels on the Digital Array were used for each DNA sample, which corresponded to 4590 individual PCRs. The reaction for one sample (6 panels) was set up using 2×TaqMan Universal PCR Master Mix (Applied Biosystems) in a reaction volume of 52 µL. The reactions were set up according to the manufacturer's protocol with the primer and probe compositions listed in table 1000 of FIG. 10. Each reaction mix contained 18.2 µL of the DNA sample. The reaction mixture was automatically loaded onto the Digital Array by the NanoFlex IFC Controller (Fluidigm). The reactions were carried out on the BioMark System (Fluidigm). The reactions were initiated at 50° C. for 2 minutes, followed by 95° C. for 10 minutes, and 45 cycles of 95° C. for 15 seconds and assay-specific annealing temperatures (FIG. 10 TABLE 3) for 1 minute. For a sample that remained unclassified by the RMD with data from one 4590-well digital PCR set, additional 4590-well digital PCR sets were carried out until a genotype call could be made.

Results

Principle of Digital RMD for X-Linked Polymorphisms

Embodiments can use digital PCR to measure the concentration difference between the total amount (maternal-plus fetal-derived) of mutant and wild-type alleles in the plasma of heterozygous pregnant women carrying male fetuses. Since a male fetus possesses a single chromosome X, the relative concentration between the wild-type and the mutant allele is always in dosage imbalance (FIG. 2A). An over- or under-representation of the mutant allele represents an affected or normal fetus, respectively. We used SPRT to test for dosage imbalance. A pair of SPRT curves was constructed (FIG. 2B). Samples with data points above the upper curve or below the lower curve were classified as affected or normal, respectively. Samples with data points in between the two curves were not classified because of insufficient statistical power and additional digital PCRs would be performed.

Noninvasive Determination of the Fetal Genotype for a SNP on Chromosome X

We used a SNP, rs6528633 (A/T polymorphism), on chromosome X as a model to assess the practical feasibility of the RMD approach for determining the fetal genotype of a locus on chromosome X. The current RMD analysis is relevant to at-risk pregnant cases, i.e., pregnant women who are heterozygous for mutations on chromosome X and are carrying male fetuses. Hence, we studied the plasma samples from ten pregnant women who were heterozygous for the SNP on chromosome X and were carrying male fetuses. We developed an allele-discriminative digital real-time PCR assay to measure the concentrations of the A- and T-allele in each sample. We further measured the fractional fetal DNA concentrations with the ZFY/X assay. The digital RMD result is shown in table 1100 of FIG. 11, which shows fetal genotyping for rs6528633 in maternal plasma by digital RMD.

For all of the cases, the fetal SNP genotypes were concordant with the SPRT classification. The fractional fetal DNA concentrations (fetal % in table 1100) ranged from 5% to 24%. The result hence confirmed the feasibility of the digital RMD strategy.

Digital RMD for Hemophilia Mutation Detection in DNA Mixtures

We next applied the digital RMD approach for hemophilia mutation detection. We developed seven duplex digital real-time PCR assays to detect three mutations in the F8 gene, four mutations in the F9 gene and their corresponding wild-type counterparts. We evaluated the performance of the digital PCR assays by constructing artificial DNA mixtures that simulated the composition of maternal plasma samples with a minority male fetal DNA component amongst a majority maternal DNA background. We mixed 10% or 20% of placental DNA obtained from an unaffected male fetus with blood cell DNA obtained from women heterozygous for the corresponding mutations. FIG. 12 shows the validation of digital RMD assays with artificial DNA mixtures. The artificial mixtures were constructed to simulate the fetal and maternal DNA compositions in maternal plasma. As shown in table 1200 of FIG. 12, the genotypes of the placental DNA, which mimicked the fetal DNA in maternal plasma, were correctly detected in all of the DNA mixtures by digital RMD analysis.

Detection of Fetal Hemophilia Mutations in Maternal Plasma

We tested the digital RMD method for detecting fetal genotypes for the hemophilia mutations through maternal plasma DNA analysis. We carried out digital PCR on 12 plasma samples obtained from seven pregnant women heterozygous for the causative mutations (TABLE 900). All of the cases involved male fetuses. We also measured the fractional fetal DNA concentrations in the maternal plasma samples by the ZFY/X assay. The digital RMD results are shown in table 1300 of FIG. 13, which shows non-invasive detection of fetal hemophilia mutations in maternal plasma by digital RMD.

Figure 14:
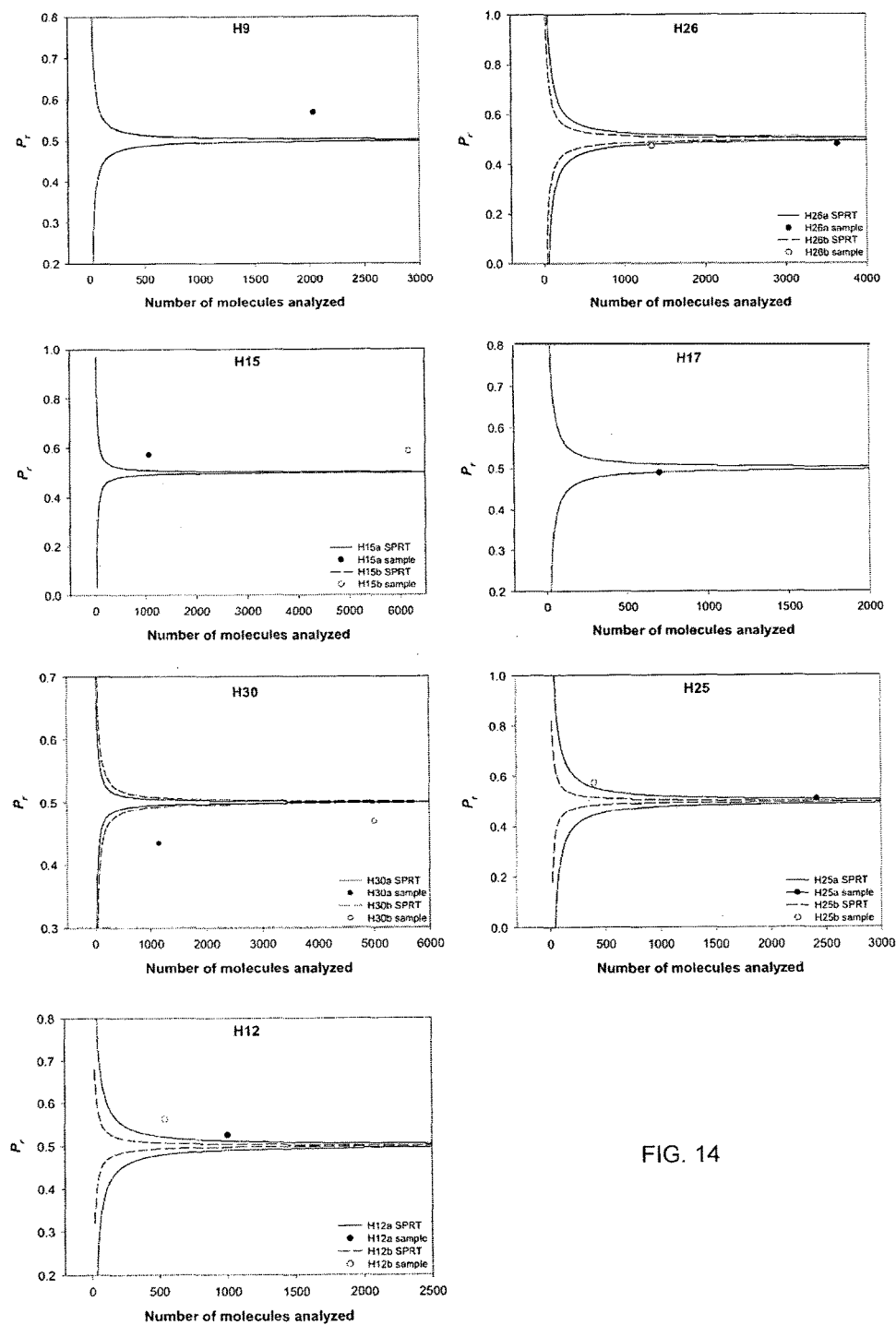
FIG. 14 shows plots of SPRT analysis for fetal hemophilia mutations in maternal plasma samples. Case numbers are indicated at the top of the graphs. $P_r$, proportion of positive wells containing the mutant allele.

The fetal genotypes were correctly classified in all studied cases by the SPRT algorithm (FIG. 14). For three of the cases (H26a, H25a and H12a), the fetal DNA proportions were less than 10%. Hence, the degree of quantitative difference between the amount of mutant and the wild-type alleles was too small to be classified with data from one 4590-well digital PCR set. Additional 4590-well digital PCR sets were therefore performed until classifications could be made.

As controls, we also studied five maternal plasma samples obtained from normal pregnant women using each of the mutation-specific assays. FIG. 15 shows digital RMD result for maternal plasma samples from normal pregnancies. As shown in table 1500 of FIG. 15, no mutant alleles were detected in most of the cases. For six of the 35 studied maternal plasma cases, the positive wells containing the mutant alleles constituted less than 0.3% of the total number of positive wells in the experiments. These positive signals might have resulted from cross hybridizations of the fluorescent probes during PCR. Nonetheless, such low numbers of mutant-positive wells would not skew the allelic ratio between mutant and wild-type alleles to an extent that would alter the RMD classification by SPRT.

Discussion

In this study, we have developed noninvasive prenatal diagnostic strategies to directly detect causative mutations carried by male fetuses in pregnancies at-risk of X-linked diseases, using hemophilia as an example. By using the digital RMD approach for genetic loci on chromosome X, we have accurately identified the mutant or the wild-type alleles inherited by the male fetuses in all of the 12 studied maternal plasma samples from seven pregnant carriers of hemophilia (table 1300). The fetal genotypes could be detected as early as the 11$^{th}$ week of gestation (table 900), demonstrating the potential for early diagnostic use of the method. The approach using a target region and a reference region on chromosome X can also be used.

This noninvasive prenatal mutation detection method could be combined with the existing noninvasive fetal sex determination test to further minimize the number of at-risk pregnant cases that would require invasive diagnostic testing. The identification of affected fetuses could also facilitate subsequent obstetric management for pregnant women who would not otherwise consider invasive prenatal testing. Three to four percent of infants with hemophilia experience a cranial bleed (Kulkarni R, Lusher J M., *J Pediatr Hematol Oncol.*, 21:289-295 (1999)) that occurs during labor and delivery. Prolonged labor and difficult instrumental deliveries are the main risk factors for this complication (Kadir R A et al., *Haemophilia.*, 6:33-40 (2000); Chi C et al., *Haemophilia.*, 14:56-64 (2008)) and should be avoided for delivery of affected fetuses (Lee C A, Chi C, Pavord S R, et al., *Haemophilia.*, 12:301-336 (2006)). It is also recommended that affected fetuses are delivered in a tertiary unit with an affiliated hemophilia center to ensure availability of necessary expertise and resources for their management (Lee C A, Chi C, Pavord S R, et al., *Haemophilia.*, 12:301-336 (2006)). Recently, prenatal diagnosis by third trimester amniocentesis has been suggested to help appropriate planning of the mode and place of delivery for parents who are unwilling to accept the risk of fetal loss associated with earlier prenatal testing (Chi C, Kadir R A., Obstetric Management. In: Lee C A, Kadir R A, Kouides P A, eds. *Inherited Bleeding Disorders in Women*, Chichester, West Sussex, UK: Wiley-Blackwell, 122-148 (2009)). If a fetus is unaffected, labor and delivery can be managed without any restrictions in local maternity units. However, third trimester amniocentesis is also an invasive procedure and associated with potential risks and complications (Hodor J G, Poggi S H, Spong C Y, et al., *Am J Perinatol.*, 23:177-180 (2006); O'Donoghue K et al., *Prenat Diagn.*, 27:1000-1004 (2007)). Fetal DNA concentration is the highest during the third trimester of pregnancy (Lun F M F et al., *Clin Chem.*, 54:1664-1672 (2008)), thus embodiments can offer an accurate noninvasive alternative to third trimester amniocentesis for this purpose.

VII. Computer System

Figure 16:
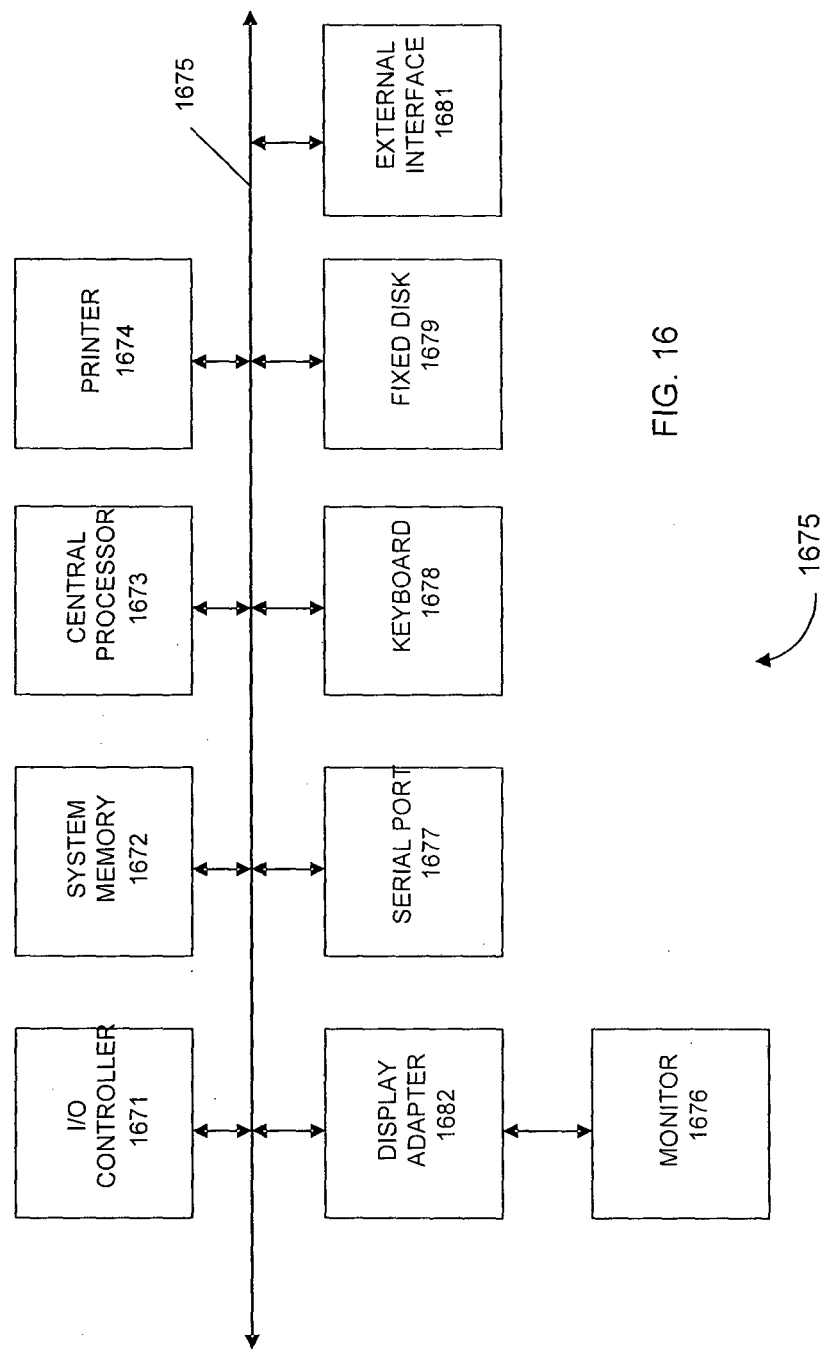
FIG. 16 shows a block diagram of an example computer system 1600 usable with system and methods according to embodiments of the present invention.

Any of the computer systems mentioned herein may utilize any suitable number of subsystems. Examples of such subsystems are shown in FIG. 16 in computer apparatus 1600. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 16 are interconnected via a system bus 1675. Additional subsystems such as a printer 1674, keyboard 1678, fixed disk 1679, monitor 1676, which is coupled to display adapter 1682, and others are shown. Peripherals and input/output (I/O) devices, which couple to I/O controller 1671, can be connected to the computer system by any number of means known in the art, such as serial port 1677. For example, serial port 1677 or external interface 1681 can be used to connect computer system 1600 to a wide area network such as the Internet, a mouse input device, or a scanner. The interconnection via system bus 1675 allows the central processor 1673 to communicate with each subsystem and to control the execution of instructions from system memory 1672 or the fixed disk 1679, as well as the exchange of information between subsystems. The system memory 1672 and/or the fixed disk 1679 may embody a computer readable medium. Any of the values mentioned herein can be output from one component to another component and can be output to the user.

A computer system can include a plurality of the same components or subsystems, e.g., connected together by external interface 1681 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method for determining whether a male fetus of a pregnant female has an X-linked mutation, wherein the pregnant female is heterozygous for a mutant and a normal allele at a locus on the X chromosome, the method comprising:

performing a plurality of reactions, each involving one or more nucleic acid molecules from a biological sample, the biological sample including cell-free nucleic acid molecules from the pregnant female and from the male fetus;

detecting data from the plurality of reactions, receiving, by a computer system, the data from the plurality of reactions, wherein the data includes:
  a first set of quantitative data indicating a first amount of the mutant allele at the locus; and
  a second set of quantitative data indicating a second amount of the normal allele at the locus;

determining, by the computer system, a parameter from the first amount and the second amount, wherein the parameter represents a relative amount between the first and second amounts;

obtaining, by the computer system, a percentage Pf of fetal nucleic acid molecules in the biological sample;

calculating, by the computer system, a first cutoff value for determining whether the fetus has inherited the mutant allele at the locus, wherein the first cutoff value is derived at least from a first proportion of $k/(1+k-Pf)$, where k is a number of mutant alleles on a mutant chromosome of the pregnant female, k being an integer equal to or greater than one;

calculating, by the computer system, a second cutoff value for determining whether the fetus has inherited the normal allele at the locus, wherein the second cutoff value is derived at least from a second proportion of $[k(1-Pf)]/[1+k-kPf]$; and comparing, by the computer system, the parameter to at least one of the first and second cutoff values to determine a classification of whether the fetus has inherited the mutant allele or the normal allele.

2. The method of claim 1, wherein the parameter is compared to the first and second cutoff values.

3. The method of claim 2 wherein the classifications include disease state, non-disease state, and non-classifiable.

4. The method of claim 1, wherein obtaining the percentage Pf includes:
correcting an experimentally derived percentage of fetal nucleic acid molecules in the biological sample with an expected statistical distribution of molecules in the plurality of reactions.

5. The method of claim 1, wherein obtaining the percentage Pf includes:

detecting a first allele in the reactions, wherein the first allele is shared by the mother and fetus at a locus where the pregnant female is homozygous and the fetus is either heterozygous or hemizygous;

calculating a Poisson-corrected concentration Px with the equation $[-\ln((N-P1)/N)]*N$, where N is the total number of reactions analyzed, P1 is the number of reactions positive for the first allele, and ln is the natural logarithm;

detecting a second allele in the reactions, wherein the second allele is specific to the fetus; and calculating a Poisson-corrected concentration Py with the equation $[-\ln((N-P2)/N)]*N$ where N is the total number of reactions analyzed, and P2 is the number of reactions positive for the second allele.

6. The method of claim 5, wherein the second allele is on chromosome Y.

7. The method of claim 5, wherein the first allele is on chromosome X.

8. The method of claim 5, wherein the fetal-specific allele is a paternally-inherited allele on an autosome.

9. The method of claim 5, wherein the fetal-specific allele includes a methylation marker specific to the fetus.

10. The method of claim 5, further comprising:
calculating Pf as $[(2Py)/(Px+Py)]*100\%$.

11. The method of claim 1, wherein the first and second cutoff values are determined using a sequential probability ratio test (SPRT) to determine whether the fetus has inherited the mutant or the normal nucleic acid sequence.

12. The method of claim 1, wherein an allele at a polymorphic site linked to the mutant allele is located on the same maternal haplotype as the mutant allele, and wherein the probability of recombination between the polymorphic site and the mutant allele is less than 1%.

13. The method of claim 1, wherein an allele at a polymorphic site linked to the normal allele is located on the same maternal haplotype as the normal allele, and wherein the probability of recombination between the polymorphic site and the mutant allele is less than 1%.

14. The method of claim 1, wherein the reactions include any one or more of the following: sequencing reactions, optical analysis, and hybridization using a fluorescent probe, or nanopore sequencing.

15. The method of claim 1, wherein a reaction is an amplification reaction.

16. The method of claim 15, wherein the reactions include polymerase chain reactions.

17. The method of claim 15, wherein an average concentration is less than one template molecule per reaction, and wherein a Poisson distribution is used in determining the percentage Pf of fetal nucleic acid molecules in the biological sample.

18. The method of claim 1, wherein the biological sample is plasma, serum, or whole blood from a pregnant woman.

19. A computer program product comprising a non-transitory computer readable medium storing a plurality of instructions for controlling an apparatus to perform the method of claim 1.

20. The method of claim 1, further comprising:
displaying, by the computer system, the classification of whether the fetus has inherited the mutant allele or the normal allele based on comparing the parameter to at least one of the first and second cutoff values.

21. The method of claim 1, wherein performing the plurality of reactions and detecting the data comprises:
receiving a blood sample from the female;
collecting plasma or serum from the blood sample to obtain the biological sample;
sequencing the nucleic acid molecules from the plasma or serum using the plurality of reactions to obtain sequence tags;
aligning, by a computer system, sequence tags to a reference genome to identify tags aligning to the mutant allele at the locus;
aligning, by a computer system, sequence tags to the reference genome to identify tags aligning to the normal allele at the locus;
measuring, by the computer system, the first amount of the mutant allele by counting the number of tags aligning to the mutant allele at the locus; and
measuring, by the computer system, the second amount of the normal allele by counting the number of tags aligning to the normal allele at the locus.

22. The method of claim 21, wherein the X-linked mutation is a mutation related to hemophilia, and
the method further comprising:
determining the fetus has inherited the mutant allele, and
treating the male fetus or the pregnant female to decrease the risk of fetal and neonatal hemorrhagic complications.

23. The method of claim 1, wherein the plurality of reactions is at least 1,000 reactions.

24. The method of claim 1, further comprising:
determining the fetus has inherited the mutant allele, and
treating the male fetus or the pregnant female to decrease the risk of fetal and neonatal complications.

25. The method of claim 1, wherein the X-linked mutation is a mutation related to hemophilia, Duchenne muscular dystrophy, X-linked adrenoleukodystrophy, Becker muscular dystrophy, choroideremia, Hunter syndrome, Lesch Nyhan syndrome, Norrie's syndrome, or ornithine transcarbamylase deficiency.

26. The method of claim 1, wherein the X-linked mutation is a mutation related to hemophilia, and
the method further comprising:
determining the fetus has inherited the mutant allele, and
treating the male fetus or the pregnant female to decrease the risk of fetal and neonatal hemorrhagic complications.

27. The method of claim 1, wherein the first amount is less than 1160, and the method further comprises determining the fetus has inherited the mutant allele.

28. The method of claim 1, wherein:
the plurality of reactions is a first plurality of reactions, and
the parameter is a first parameter;
the method further comprising:
determining based on the first cutoff value and the second cutoff value that the fetus cannot be classified as inheriting the mutant allele and cannot be classified as inheriting the normal allele;
performing a second plurality of reactions;
detecting data from a second plurality of reactions;
receiving, by the computer system, the data from the second plurality of reactions, each reaction involving one or more nucleic acid molecules from the biological sample, wherein data from each of the one or more second pluralities of reactions includes:

a third set of quantitative data indicating a third amount of the mutant allele at the locus; and a fourth set of quantitative data indicating a fourth amount of the normal allele at the locus;

determining, by the computer system, a second parameter from the first amount, the second amount, the third amount, and the fourth amount, wherein the second parameter represents a relative amount between the sum of the first amount and the third amount and the sum of the second amount and the fourth amount;

comparing, by the computer system, the second parameter to at least one of the first and second cutoff values to classify the fetus as inheriting either the mutant allele or the normal allele.

29. The method of claim 28, wherein the first plurality of reactions and the second plurality of reactions total to less than or equal to 13,770 reactions.

30. The method of claim 29, wherein:

updating the first cutoff value comprises using sequential probability ratio test (SPRT), and updating the second cutoff value comprises using SPRT.

31. The method of claim 29, wherein the X-linked mutation is a mutation related to hemophilia, and the method further comprising:

determining the fetus has inherited the mutant allele, and treating the male fetus or the pregnant female to decrease the risk of fetal and neonatal hemorrhagic complications.

32. The method of claim 28, wherein:

the first cutoff value is based on a total number of reactions, and the second cutoff value is based on the total number of reactions, the method further comprising:

updating the first cutoff value based on a total number of the first plurality of reactions and the second plurality of reactions, and updating the second cutoff value based on the total number of the first plurality of reactions and the second plurality of reactions.

33. The method of claim 28, wherein:

performing the first plurality of reactions comprises using one or more primers and/or probes specific to the X chromosome.

34. A method for determining whether a male fetus of a pregnant female has an X-linked mutation, the method comprising:

receiving a blood sample from the pregnant female;

collecting plasma or serum from the blood sample to obtain a biological sample, the biological sample including cell-free nucleic acid molecules from the pregnant female and from the male fetus, wherein the pregnant female is homozygous for an allele at a locus on the X chromosome, has a mutation of an amplification of the allele on a mutant X chromosome, the mutant X chromosome having a normal copy of the allele at the locus and one or more additional copies of the allele, and has a normal X chromosome having a normal copy of the allele at the locus;

sequencing the nucleic acid molecules from the plasma or serum using a plurality of reactions to obtain sequence tags, each reaction of the plurality of reactions involving one or more nucleic acid molecules from the biological sample;

measuring, by a computer system, a first amount of an additional junction created by the one or more additional copies of the allele, wherein measuring comprises counting the number of tags aligning to the additional junction;

measuring, by the computer system, a second amount of a normal junction created by the normal copy of the allele on both X chromosomes, wherein measuring comprises counting the number of tags aligning to the normal junction;

determining, by the computer system, a parameter from the first amount and the second amount, wherein the parameter represents a relative amount between the first and second amounts;

obtaining, by the computer system, a percentage Pf of fetal nucleic acid molecules in the biological sample;

calculating, by the computer system, a first cutoff value for determining whether the fetus has inherited the mutant X chromosome, wherein the first cutoff value is derived at least from a first proportion of $n/(n+1-Pf)$, where n is the number of additional copies of the allele, n being an integer equal to or greater than one;

calculating, by the computer system, a second cutoff value for determining whether the fetus has inherited the normal X chromosome, wherein the second cutoff value is derived at least from a second proportion of $[n(1-Pf)/[n+2-Pf(n+1)]$; and comparing, by the computer system, the parameter to at least one of the first and second cutoff values to determine a classification of whether the fetus has inherited the mutant X chromosome or the normal X chromosome.

35. The method of claim 34, further comprising:

determining the fetus has inherited the mutant X chromosome, wherein the mutant X chromosome is related to hemophilia; and treating the male fetus or the pregnant female to decrease the risk of fetal and neonatal hemorrhagic complications.

36. A method for determining whether a male fetus of a pregnant female has an X-linked mutation, wherein the pregnant female is heterozygous for a mutation and a normal allele at a target region on the X chromosome, wherein the mutation is a deletion or an amplification of the target region, the method comprising:

receiving a blood sample from the pregnant female;

collecting plasma or serum from the blood sample to obtain a biological sample, the biological sample including cell-free nucleic acid molecules from the pregnant female and from the male fetus;

sequencing the nucleic acid molecules from the plasma or serum using a plurality of reactions to obtain sequence tags, each reaction of the plurality of reactions involving one or more nucleic acid molecules from the biological sample;

aligning, by a computer system, sequence tags to a reference genome to identify tags aligning to the target region;

aligning, by a computer system, sequence tags to a reference genome to identify tags aligning to the reference region on the X chromosome;

measuring, by the computer system, a first amount of the nucleic acid molecules that are from the target region, wherein measuring comprises counting the number of tags aligning to the target region;

measuring, by the computer system, a second amount of the nucleic acid molecules that are from a reference region on the X chromosome, wherein measuring comprises counting the number of tags aligning to the reference region;

determining, by the computer system, a parameter from the first amount and the second amount, wherein the parameter represents a relative amount between the first and second amounts;

obtaining, by the computer system, a percentage Pf of fetal nucleic acid molecules in the biological sample;

calculating, by the computer system, a first cutoff value for determining whether the fetus has inherited the mutation, the first cutoff value being dependent on the percentage Pf;

calculating, by the computer system, a second cutoff value for determining whether the fetus has inherited the normal allele, the second cutoff value being dependent on the percentage Pf; and comparing, by the computer system, the parameter to at least one of the first and second cutoff values to determine a classification of whether the fetus has inherited the mutation or the normal allele.

37. The method of claim 36, wherein the mutation is an amplification, wherein the first cutoff value is determined based on the assumption that a ratio of the first amount to the second amount is increased when compared with a corresponding ratio of a non-pregnant woman carrying the same amplification mutation, and the second cutoff value is based on the assumption that the ratio of the first amount to second amount is decreased when compared with the corresponding ratio of a non-pregnant woman carrying the same amplification mutation.

38. The method of claim 36, wherein the mutation is a deletion, wherein the second cutoff value is determined based on the assumption that a ratio of the first amount to the second amount is increased when compared with a corresponding ratio of a non-pregnant woman carrying the same deletion mutation, and the first cutoff value is based on the assumption that the ratio of the first amount to the second amount is decreased when compared with the corresponding ratio of a non-pregnant woman carrying the same deletion mutation.

39. The method of claim 36, wherein the mutation is a deletion, wherein the second cutoff value is derived at least from a first proportion of $1/(2-Pf)$, and wherein the first cutoff value is derived at least from a second proportion of $(1-Pf)/(2-Pf)$.

40. The method of claim 36, wherein the mutation is a duplication, wherein the second cutoff value is derived at least from a first proportion of $(3-Pf)/(2-Pf)$, and wherein the first cutoff value is derived at least from a second proportion of $(3-2Pf)/(2-Pf)$.

41. The method of claim 36, wherein obtaining the percentage Pf includes:
correcting an experimentally derived percentage of fetal nucleic acid molecules in the biological sample with an expected statistical distribution of molecules in the plurality of reactions.

42. The method of claim 36, further comprising:
determining the fetus has inherited the mutation, wherein the mutation is related to hemophilia; and
treating the male fetus or the pregnant female to decrease the risk of fetal and neonatal hemorrhagic complications.

43. A method of obtaining a percentage Pf of fetal nucleic acid molecules in a biological sample from a female pregnant with a fetus, the method comprising:

receiving a blood sample from the female;
collecting plasma or serum from the blood sample to obtain the biological sample, the biological sample including cell-free nucleic acid molecules from the pregnant female and from the fetus;
sequencing the nucleic acid molecules from the plasma or serum using a plurality of reactions to obtain sequence tags, each reaction of the plurality of reactions involving a plurality of nucleic acid molecules from a biological sample, the biological sample including cell-free nucleic acid molecules from the pregnant female and from the fetus;
receiving, by the computer system, data from a plurality of reactions, the data including the sequence tags;
detecting, by the computer system, a first allele in the reactions, wherein the first allele is shared by the mother and fetus at a locus where the pregnant female is homozygous and the fetus is either heterozygous or hemizygous, wherein detecting the first allele comprises aligning sequence tags to a reference genome to identify tags aligning to the first allele;
calculating, by the computer system, a corrected concentration Px of the first allele based on a number of reactions positive for the first allele, where Px is corrected for an expected statistical distribution of the first allele in the plurality of reactions;
detecting, by the computer system, a second allele in the reactions, wherein the second allele is specific to the fetus, wherein detecting the second allele comprises aligning sequence tags to a reference genome to identify tags aligning to the second allele;
calculating, by the computer system, a corrected concentration Py of the second allele based on a number of reactions positive for the second allele, where Py is corrected for an expected statistical distribution of the second allele in the plurality of reactions; and
calculating, by the computer system, Pf using $[(2Py)/(Px+Py)]$.

44. The method of claim 43, wherein Pf equals $[(2Py)*(Px+Py)]*100\%$.

45. The method of claim 43, wherein the statistical distribution is Poisson, and wherein the Poisson-corrected concentration Px uses the equation $[-\ln((N-P1)/N)]*N$ where N is the total number of reactions analyzed, P1 is the number of reactions positive for the first allele, and ln is the natural logarithm, and wherein the Poisson-corrected concentration Py uses the equation $[-\ln((N-P2)/N)]*N$, where N is the total number of reactions analyzed, and P2 is the number of reactions positive for the second allele.

46. The method of claim 43, wherein the data includes:
a first set of quantitative data indicating a first amount of an allele at a polymorphic site linked to the first allele; and
a second set of quantitative data indicating a second amount of an allele at a polymorphic site linked to the second allele, the method further comprising:
determining a parameter from the two data sets;
determining a first cutoff value for determining whether the fetus has inherited a mutant nucleic acid sequence, wherein the first cutoff value is determined based on the percentage Pf;
determining a second cutoff value for determining whether the fetus has inherited the normal nucleic acid sequence, wherein the second cutoff value is determined based on the percentage Pf;
comparing the parameter to at least one of the first and second cutoff values; and based on the comparison, determining a classification of whether the fetus has inherited the mutant or the normal nucleic acid sequence.

47. A method for determining whether a male fetus of a pregnant female has an X-linked mutation, the method comprising:
receiving, by a computer system, data from a plurality of reactions, each involving one or more nucleic acid molecules from a biological sample, the biological sample including cell-free nucleic acid molecules from the pregnant female and from the male fetus,
wherein the pregnant female is homozygous for an allele at a locus on the X chromosome, has a mutation of an amplification of the allele on a mutant X chromosome, the mutant X chromosome having a normal copy of the allele at the locus and one or more additional copies of the allele, and has a normal X chromosome having a normal copy of the allele at the locus,
wherein the data includes:
a first set of quantitative data indicating a first amount of an additional junction created by the one or more additional copies of the allele; and
a second set of quantitative data indicating a second amount of a normal junction created by the normal copy of the allele on both X chromosomes;
determining, by the computer system, a parameter from the first amount and the second amount, wherein the parameter represents a relative amount between the first and second amounts;
obtaining, by the computer system, a percentage Pf of fetal nucleic acid molecules in the biological sample;
calculating, by the computer system, a first cutoff value for determining whether the fetus has inherited the mutant X chromosome, wherein the first cutoff value is derived at least from a first proportion of $n/(n+1-Pf)$, where n is the number of additional copies of the allele, n being an integer equal to or greater than one;
calculating, by the computer system, a second cutoff value for determining whether the fetus has inherited the normal X chromosome, wherein the second cutoff value is derived at least from a second proportion of $[n(1-Pf)/[n+2-Pf(n+1)]$;
comparing, by the computer system, the parameter to at least one of the first and second cutoff values to determine a classification of whether the fetus has inherited the mutant X chromosome or the normal X chromosome;
determining the fetus has inherited the mutant X chromosome, wherein the mutant X chromosome is related to hemophilia; and
treating the male fetus or the pregnant female to decrease the risk of fetal and neonatal hemorrhagic complications.

48. A method for determining whether a male fetus of a pregnant female has an X-linked mutation, wherein the pregnant female is heterozygous for a mutation and a normal allele at a target region on the X chromosome, wherein the mutation is a deletion or an amplification of the target region, the method comprising:
receiving, by a computer system, data from a plurality of reactions, each involving one or more nucleic acid molecules from a biological sample, the biological sample including cell-free nucleic acid molecules from the pregnant female and from the male fetus, wherein the data includes:
a first set of quantitative data indicating a first amount of the nucleic acid molecules that are from the target region; and
a second set of quantitative data indicating a second amount of the nucleic acid molecules that are from a reference region on the X chromosome;
determining, by the computer system, a parameter from the first amount and the second amount, wherein the parameter represents a relative amount between the first and second amounts;
obtaining, by the computer system, a percentage Pf of fetal nucleic acid molecules in the biological sample;
calculating, by the computer system, a first cutoff value for determining whether the fetus has inherited the mutation, the first cutoff value being dependent on the percentage Pf;
calculating, by the computer system, a second cutoff value for determining whether the fetus has inherited the normal allele, the second cutoff value being dependent on the percentage Pf;
comparing, by the computer system, the parameter to at least one of the first and second cutoff values to determine a classification of whether the fetus has inherited the mutation or the normal allele;
determining the fetus has inherited the mutation, wherein the mutation is related to hemophilia; and
treating the male fetus or the pregnant female to decrease the risk of fetal and neonatal hemorrhagic complications.

49. A system for determining whether a male fetus of a pregnant female has an X-linked mutation, wherein the pregnant female is heterozygous for a mutant and a normal allele at a locus on the X chromosome, the system comprising:
a platform configured to:
perform a plurality of reactions, each involving one or more nucleic acid molecules from a biological sample, the biological sample including cell-free nucleic acid molecules from the pregnant female and from the male fetus, and
detect data from the plurality of reactions; and
a computer system comprising a non-transitory computer readable medium storing a plurality of instructions for controlling a processor to perform an operation, the instructions comprising:
receiving the data from the plurality of reactions, wherein the data includes:
a first set of quantitative data indicating a first amount of the mutant allele at the locus; and
a second set of quantitative data indicating a second amount of the normal allele at the locus;
determining a parameter from the first amount and the second amount, wherein the parameter represents a relative amount between the first and second amounts;
obtaining a percentage Pf of fetal nucleic acid molecules in the biological sample;
calculating a first cutoff value for determining whether the fetus has inherited the mutant allele at the locus, wherein the first cutoff value is derived at least from a first proportion of $k/(1+k-Pf)$, where k is a number of mutant alleles on a mutant chromosome of the pregnant female, k being an integer equal to or greater than one;
calculating a second cutoff value for determining whether the fetus has inherited the normal allele at the locus, wherein the second cutoff value is derived at least from a second proportion of $[k(1-Pf)]/[1+k-kPf]$; and comparing the parameter to at least one of the first and second cutoff values to determine a classification of whether the fetus has inherited the mutant allele or the normal allele.

* * * * *

UNITED STATES PATENT AND TRADEMARK OFFICE
CERTIFICATE OF CORRECTION

PATENT NO. : 10,152,568 B2
APPLICATION NO. : 13/978358
DATED : December 11, 2018
INVENTOR(S) : Yuk Ming Dennis Lo et al.

It is certified that error appears in the above-identified patent and that said Letters Patent is hereby corrected as shown below:

In the Claims

In Column 43, Line 8 of Claim 5, please delete "and In is the natural" and insert --and ln is the natural--

In Column 43, Line 13 of Claim 5, please delete "*N where N" and insert --*N, where N--

In Column 48, Line 1 of Claim 44, please delete "[(2Py)*" and insert --[(2Py)/--

In Column 48, Line 3 of Claim 45, please delete "*N" and insert --*N,--

In Column 48, Line 5 of Claim 45, please delete "and In is the" and insert --and ln is the--

Signed and Sealed this
Twenty-first Day of January, 2020

Andrei Iancu
*Director of the United States Patent and Trademark Office*

SEQUENCE LISTING

```
<160> NUMBER OF SEQ ID NOS: 36

<210> SEQ ID NO 1
<211> LENGTH: 25
<212> TYPE: DNA
<213> ORGANISM: Artificial Sequence
<220> FEATURE:
<223> OTHER INFORMATION: synthetic locus ZFY/X direct PCR
      oligonucleotide F-primer

<400> SEQUENCE: 1
caagtgctgg actcagatgt aactg                                           25
```

```
<210> SEQ ID NO 2
<211> LENGTH: 28
<212> TYPE: DNA
<213> ORGANISM: Artificial Sequence
<220> FEATURE:
<223> OTHER INFORMATION: synthetic locus ZFY/X direct PCR
      oligonucleotide R-primer

<400> SEQUENCE: 2
tgaagtaatg tcagaagcta aaacatca                                           28

<210> SEQ ID NO 3
<211> LENGTH: 16
<212> TYPE: DNA
<213> ORGANISM: Artificial Sequence
<220> FEATURE:
<223> OTHER INFORMATION: synthetic locus ZFY/X X-probe
<220> FEATURE:
<221> NAME/KEY: modified_base
<222> LOCATION: (1)..(1)
<223> OTHER INFORMATION: t modified by fluorescent reporter dye VIC
<220> FEATURE:
<221> NAME/KEY: modified_base
<222> LOCATION: (16)..(16)
<223> OTHER INFORMATION: a modified by minor groove binding
      nonfluorescent quencher (MGBNFQ)

<400> SEQUENCE: 3
tctttagcac attgca                                                        16

<210> SEQ ID NO 4
<211> LENGTH: 17
<212> TYPE: DNA
<213> ORGANISM: Artificial Sequence
<220> FEATURE:
<223> OTHER INFORMATION: synthetic locus ZFY/X Y-probe
<220> FEATURE:
<221> NAME/KEY: modified_base
<222> LOCATION: (1)..(1)
<223> OTHER INFORMATION: t modified by luorescent reporter dye FAM
<220> FEATURE:
<221> NAME/KEY: modified_base
<222> LOCATION: (17)..(17)
<223> OTHER INFORMATION: c modified by minor groove binding
      nonfluorescent quencher (MGBNFQ)

<400> SEQUENCE: 4
tctttaccac actgcac                                                       17

<210> SEQ ID NO 5
<211> LENGTH: 23
<212> TYPE: DNA
<213> ORGANISM: Artificial Sequence
<220> FEATURE:
<223> OTHER INFORMATION: synthetic locus SNP rs6528633 direct PCR
      oligonucleotide F-primer

<400> SEQUENCE: 5
ggaagaccaa aaagggataa agg                                                23

<210> SEQ ID NO 6
<211> LENGTH: 21
<212> TYPE: DNA
<213> ORGANISM: Artificial Sequence
<220> FEATURE:
<223> OTHER INFORMATION: synthetic locus SNP rs6528633 direct PCR
      oligonucleotide R-primer

<400> SEQUENCE: 6
``` cacccctactc ccagccaatt t                                              21

<210> SEQ ID NO 7
<211> LENGTH: 20
<212> TYPE: DNA
<213> ORGANISM: Artificial Sequence
<220> FEATURE:
<223> OTHER INFORMATION: synthetic locus SNP rs6528633 T-probe
<220> FEATURE:
<221> NAME/KEY: modified_base
<222> LOCATION: (1)..(1)
<223> OTHER INFORMATION: t modified by fluorescent reporter dye VIC
<220> FEATURE:
<221> NAME/KEY: modified_base
<222> LOCATION: (20)..(20)
<223> OTHER INFORMATION: g modified by minor groove binding
      nonfluorescent quencher (MGBNFQ)

<400> SEQUENCE: 7
tgagatatga tatggtcatg                                                 20

<210> SEQ ID NO 8
<211> LENGTH: 20
<212> TYPE: DNA
<213> ORGANISM: Artificial Sequence
<220> FEATURE:
<223> OTHER INFORMATION: synthetic locus SNP rs6528633 A-probe
<220> FEATURE:
<221> NAME/KEY: modified_base
<222> LOCATION: (1)..(1)
<223> OTHER INFORMATION: t modified by fluorescent reporter dye FAM
<220> FEATURE:
<221> NAME/KEY: modified_base
<222> LOCATION: (20)..(20)
<223> OTHER INFORMATION: g modified by minor groove binding
      nonfluorescent quencher (MGBNFQ)

<400> SEQUENCE: 8
tgagatatga taaggtcatg                                                 20

<210> SEQ ID NO 9
<211> LENGTH: 20
<212> TYPE: DNA
<213> ORGANISM: Artificial Sequence
<220> FEATURE:
<223> OTHER INFORMATION: synthetic locus F8 c.826G>A direct PCR
      oligonucleotide F-primer

<400> SEQUENCE: 9
tggatgccac aggaaatcag                                                 20

<210> SEQ ID NO 10
<211> LENGTH: 20
<212> TYPE: DNA
<213> ORGANISM: Artificial Sequence
<220> FEATURE:
<223> OTHER INFORMATION: synthetic locus F8 c.826G>A direct PCR
      oligonucleotide R-primer

<400> SEQUENCE: 10
cttcaggagt ggtgcccatt                                                 20

<210> SEQ ID NO 11
<211> LENGTH: 17
<212> TYPE: DNA
<213> ORGANISM: Artificial Sequence
<220> FEATURE:
<223> OTHER INFORMATION: synthetic locus F8 c.826G>A G-probe
<220> FEATURE:
<221> NAME/KEY: modified_base

```
<222> LOCATION: (1)..(1)
<223> OTHER INFORMATION: c modified by fluorescent reporter dye VIC
<220> FEATURE:
<221> NAME/KEY: modified_base
<222> LOCATION: (17)..(17)
<223> OTHER INFORMATION: g modified by minor groove binding
      nonfluorescent quencher (MGBNFQ)

<400> SEQUENCE: 11
ctattggcat gtgattg                                                  17

<210> SEQ ID NO 12
<211> LENGTH: 17
<212> TYPE: DNA
<213> ORGANISM: Artificial Sequence
<220> FEATURE:
<223> OTHER INFORMATION: synthetic locus F8 c.826G>A A-probe
<220> FEATURE:
<221> NAME/KEY: modified_base
<222> LOCATION: (1)..(1)
<223> OTHER INFORMATION: c modified by fluorescent reporter dye FAM
<220> FEATURE:
<221> NAME/KEY: modified_base
<222> LOCATION: (17)..(17)
<223> OTHER INFORMATION: g modified by minor groove binding
      nonfluorescent quencher (MGBNFQ)

<400> SEQUENCE: 12
ctattggcat atgattg                                                  17

<210> SEQ ID NO 13
<211> LENGTH: 22
<212> TYPE: DNA
<213> ORGANISM: Artificial Sequence
<220> FEATURE:
<223> OTHER INFORMATION: synthetic locus F8 c.1171C>T direct PCR
      oligonucleotide F-primer

<400> SEQUENCE: 13
tggatgtggt caggtttgat ga                                            22

<210> SEQ ID NO 14
<211> LENGTH: 23
<212> TYPE: DNA
<213> ORGANISM: Artificial Sequence
<220> FEATURE:
<223> OTHER INFORMATION: synthetic locus F8 c.1171C>T direct PCR
      oligonucleotide R-primer

<400> SEQUENCE: 14
ttttaggatg cttcttggca act                                           23

<210> SEQ ID NO 15
<211> LENGTH: 17
<212> TYPE: DNA
<213> ORGANISM: Artificial Sequence
<220> FEATURE:
<223> OTHER INFORMATION: synthetic locus F8 c.1171C>T C-probe
<220> FEATURE:
<221> NAME/KEY: modified_base
<222> LOCATION: (1)..(1)
<223> OTHER INFORMATION: c modifies by fluorescent reporter dye FAM
<220> FEATURE:
<221> NAME/KEY: modified_base
<222> LOCATION: (17)..(17)
<223> OTHER INFORMATION: a modified by minor groove binding
      nonfluorescent quencher (MGBNFQ)

<400> SEQUENCE: 15
ctgagcgaat ttggata                                                  17
```

<210> SEQ ID NO 16
<211> LENGTH: 16
<212> TYPE: DNA
<213> ORGANISM: Artificial Sequence
<220> FEATURE:
<223> OTHER INFORMATION: synthetic locus F8 c.1171C>T T-probe
<220> FEATURE:
<221> NAME/KEY: modified_base
<222> LOCATION: (1)..(1)
<223> OTHER INFORMATION: c modified by fluorescent reporter dye VIC
<220> FEATURE:
<221> NAME/KEY: modified_base
<222> LOCATION: (16)..(16)
<223> OTHER INFORMATION: t modified by minor groove binding
      nonfluorescent quencher (MGBNFQ)

<400> SEQUENCE: 16
ctgagcaaat ttggat                                                   16

<210> SEQ ID NO 17
<211> LENGTH: 24
<212> TYPE: DNA
<213> ORGANISM: Artificial Sequence
<220> FEATURE:
<223> OTHER INFORMATION: synthetic locus F8 c.6278A>G direct PCR
      oligonucleotide F-primer

<400> SEQUENCE: 17
tttcaggagg tagcacatac attt                                          24

<210> SEQ ID NO 18
<211> LENGTH: 20
<212> TYPE: DNA
<213> ORGANISM: Artificial Sequence
<220> FEATURE:
<223> OTHER INFORMATION: synthetic locus F8 c.6278A>G  direct PCR
      oligonucleotide R-primer

<400> SEQUENCE: 18
tgccgtgaat aatcattggt                                               20

<210> SEQ ID NO 19
<211> LENGTH: 16
<212> TYPE: DNA
<213> ORGANISM: Artificial Sequence
<220> FEATURE:
<223> OTHER INFORMATION: synthetic locus F8 c.6278A>G A-probe
<220> FEATURE:
<221> NAME/KEY: modified_base
<222> LOCATION: (1)..(1)
<223> OTHER INFORMATION: c modified by fluorescent reporter dye VIC
<220> FEATURE:
<221> NAME/KEY: modified_base
<222> LOCATION: (16)..(16)
<223> OTHER INFORMATION: c modified by minor groove binding
      nonfluorescent quencher (MGBNFQ)

<400> SEQUENCE: 19
caacagatcc acctac                                                   16

<210> SEQ ID NO 20
<211> LENGTH: 15
<212> TYPE: DNA
<213> ORGANISM: Artificial Sequence
<220> FEATURE:
<223> OTHER INFORMATION: synthetic locus F8 c.6278A>G G-probe
<220> FEATURE:
<221> NAME/KEY: modified_base
<222> LOCATION: (1)..(1)

```
<223> OTHER INFORMATION: a modified by fluorescent reporter dye FAM
<220> FEATURE:
<221> NAME/KEY: modified_base
<222> LOCATION: (15)..(15)
<223> OTHER INFORMATION: c modified by minor groove binding
      nonfluorescent quencher (MGBNFQ)

<400> SEQUENCE: 20
aacagaccca cctac                                                         15

<210> SEQ ID NO 21
<211> LENGTH: 24
<212> TYPE: DNA
<213> ORGANISM: Artificial Sequence
<220> FEATURE:
<223> OTHER INFORMATION: synthetic locus F9 c.802T>A direct PCR
      oligonucleotide F-primer

<400> SEQUENCE: 21
tctgtggagg ctctatcgtt aatg                                               24

<210> SEQ ID NO 22
<211> LENGTH: 26
<212> TYPE: DNA
<213> ORGANISM: Artificial Sequence
<220> FEATURE:
<223> OTHER INFORMATION: synthetic locus F9 c.802T>A  direct PCR
      oligonucleotide R-primer

<400> SEQUENCE: 22
acctgcgaca actgtaattt taacac                                             26

<210> SEQ ID NO 23
<211> LENGTH: 15
<212> TYPE: DNA
<213> ORGANISM: Artificial Sequence
<220> FEATURE:
<223> OTHER INFORMATION: synthetic locus F9 c.802T>A T-probe
<220> FEATURE:
<221> NAME/KEY: modified_base
<222> LOCATION: (1)..(1)
<223> OTHER INFORMATION: t modified by fluorescent reporter dye VIC
<220> FEATURE:
<221> NAME/KEY: modified_base
<222> LOCATION: (15)..(15)
<223> OTHER INFORMATION: a modified by minor groove binding
      nonfluorescent quencher (MGBNFQ)

<400> SEQUENCE: 23
tgcccactgt gttga                                                         15

<210> SEQ ID NO 24
<211> LENGTH: 15
<212> TYPE: DNA
<213> ORGANISM: Artificial Sequence
<220> FEATURE:
<223> OTHER INFORMATION: synthetic locus F9 c.802T>A A-probe
<220> FEATURE:
<221> NAME/KEY: modified_base
<222> LOCATION: (1)..(1)
<223> OTHER INFORMATION: c modified by fluorescent reporter dye FAM
<220> FEATURE:
<221> NAME/KEY: modified_base
<222> LOCATION: (15)..(15)
<223> OTHER INFORMATION: g modified by minor groove binding
      nonfluorescent quencher (MGBNFQ)

<400> SEQUENCE: 24
ctgcccacag tgttg                                                         15
```

<210> SEQ ID NO 25
<211> LENGTH: 24
<212> TYPE: DNA
<213> ORGANISM: Artificial Sequence
<220> FEATURE:
<223> OTHER INFORMATION: synthetic locus F9 c.874delC direct PCR
      oligonucleotide F-primer

<400> SEQUENCE: 25
tgtcgcaggt gaacataata ttga                                          24

<210> SEQ ID NO 26
<211> LENGTH: 25
<212> TYPE: DNA
<213> ORGANISM: Artificial Sequence
<220> FEATURE:
<223> OTHER INFORMATION: synthetic locus F9 c.874delC direct PCR
      oligonucleotide R-primer

<400> SEQUENCE: 26
ggtgaggaat aattcgaatc acatt                                         25

<210> SEQ ID NO 27
<211> LENGTH: 16
<212> TYPE: DNA
<213> ORGANISM: Artificial Sequence
<220> FEATURE:
<223> OTHER INFORMATION: synthetic locus F9 c.874delC C-probe
<220> FEATURE:
<221> NAME/KEY: modified_base
<222> LOCATION: (1)..(1)
<223> OTHER INFORMATION: a odified by fluorescent reporter dye VIC
<220> FEATURE:
<221> NAME/KEY: modified_base
<222> LOCATION: (16)..(16)
<223> OTHER INFORMATION: g modified by minor groove binding
      nonfluorescent quencher (MGBNFQ)

<400> SEQUENCE: 27
acatacagag caaaag                                                   16

<210> SEQ ID NO 28
<211> LENGTH: 15
<212> TYPE: DNA
<213> ORGANISM: Artificial Sequence
<220> FEATURE:
<223> OTHER INFORMATION: synthetic locus F9 c.874delC del-probe
<220> FEATURE:
<221> NAME/KEY: modified_base
<222> LOCATION: (1)..(1)
<223> OTHER INFORMATION: c modified by fluorescent reporter dye FAM
<220> FEATURE:
<221> NAME/KEY: modified_base
<222> LOCATION: (15)..(15)
<223> OTHER INFORMATION: c modified by minor groove binding
      nonfluorescent quencher (MGBNFQ)

<400> SEQUENCE: 28
catacagaga aaagc                                                    15

<210> SEQ ID NO 29
<211> LENGTH: 21
<212> TYPE: DNA
<213> ORGANISM: Artificial Sequence
<220> FEATURE:
<223> OTHER INFORMATION: synthetic locus F9 c.1069G>A direct PCR
      oligonucleotide F-primer

<400> SEQUENCE: 29

```
cctcaaattt ggatctggct a                                              21
```

<210> SEQ ID NO 30
<211> LENGTH: 20
<212> TYPE: DNA
<213> ORGANISM: Artificial Sequence
<220> FEATURE:
<223> OTHER INFORMATION: synthetic locus F9 c.1069G>A direct PCR
      oligonucleotide R-primer

<400> SEQUENCE: 30

```
gctgatctcc ctttgtggaa                                                20
```

<210> SEQ ID NO 31
<211> LENGTH: 16
<212> TYPE: DNA
<213> ORGANISM: Artificial Sequence
<220> FEATURE:
<223> OTHER INFORMATION: synthetic locus F9 c.1069G>A G-probe
<220> FEATURE:
<221> NAME/KEY: modified_base
<222> LOCATION: (1)..(1)
<223> OTHER INFORMATION: a modified by fluorescent reporter dye VIC
<220> FEATURE:
<221> NAME/KEY: modified_base
<222> LOCATION: (16)..(16)
<223> OTHER INFORMATION: c modified by minor groove binding
      nonfluorescent quencher (MGBNFQ)

<400> SEQUENCE: 31

```
actcttcccc agccac                                                    16
```

<210> SEQ ID NO 32
<211> LENGTH: 17
<212> TYPE: DNA
<213> ORGANISM: Artificial Sequence
<220> FEATURE:
<223> OTHER INFORMATION: synthetic locus F9 c.1069G>A A-probe
<220> FEATURE:
<221> NAME/KEY: modified_base
<222> LOCATION: (1)..(1)
<223> OTHER INFORMATION: a modified by fluorescent reporter dye FAM
<220> FEATURE:
<221> NAME/KEY: modified_base
<222> LOCATION: (17)..(17)
<223> OTHER INFORMATION: t modified by minor groove binding
      nonfluorescent quencher (MGBNFQ)

<400> SEQUENCE: 32

```
actcttctcc agccact                                                   17
```

<210> SEQ ID NO 33
<211> LENGTH: 27
<212> TYPE: DNA
<213> ORGANISM: Artificial Sequence
<220> FEATURE:
<223> OTHER INFORMATION: synthetic locus F9 c.1144T>C direct PCR
      oligonucleotide F-primer

<400> SEQUENCE: 33

```
cagtacctta gagttccact tgttgac                                        27
```

<210> SEQ ID NO 34
<211> LENGTH: 29
<212> TYPE: DNA
<213> ORGANISM: Artificial Sequence
<220> FEATURE:
<223> OTHER INFORMATION: synthetic locus F9 c.1144T>C  direct PCR
      oligonucleotide R-primer -continued

```
<400> SEQUENCE: 34
catgttgtta tagatggtga actttgtag                                29

<210> SEQ ID NO 35
<211> LENGTH: 13
<212> TYPE: DNA
<213> ORGANISM: Artificial Sequence
<220> FEATURE:
<223> OTHER INFORMATION: synthetic locus F9 c.1144T>C T-probe
<220> FEATURE:
<221> NAME/KEY: modified_base
<222> LOCATION: (1)..(1)
<223> OTHER INFORMATION: c modified by fluorescent reporter dye VIC
<220> FEATURE:
<221> NAME/KEY: modified_base
<222> LOCATION: (13)..(13)
<223> OTHER INFORMATION: g modified by minor groove binding
      nonfluorescent quencher (MGBNFQ)

<400> SEQUENCE: 35
ccacatgtct tcg                                                 13

<210> SEQ ID NO 36
<211> LENGTH: 14
<212> TYPE: DNA
<213> ORGANISM: Artificial Sequence
<220> FEATURE:
<223> OTHER INFORMATION: synthetic locus F9 c.1144T>C C-probe
<220> FEATURE:
<221> NAME/KEY: modified_base
<222> LOCATION: (1)..(1)
<223> OTHER INFORMATION: a modified by fluorescent reporter dye FAM
<220> FEATURE:
<221> NAME/KEY: modified_base
<222> LOCATION: (14)..(14)
<223> OTHER INFORMATION: c modified by minor groove binding
      nonfluorescent quencher (MGBNFQ)

<400> SEQUENCE: 36
agccacacgt cttc                                                14
```